United States Patent [19]

Ojima et al.

[11] Patent Number: 5,475,011
[45] Date of Patent: Dec. 12, 1995

[54] ANTI-TUMOR COMPOUNDS, PHARMACEUTICAL COMPOSITIONS, METHODS FOR PREPARATION THEREOF AND FOR TREATMENT

[75] Inventors: Iwao Ojima, Stony Brook, N.Y.; Ezio Bombardelli, Milan, Italy

[73] Assignee: The Research Foundation of State University of New York, Albany, N.Y.

[21] Appl. No.: 40,189

[22] Filed: Mar. 26, 1993

[51] Int. Cl.$^6$ .................. A61K 31/445; C07D 305/00
[52] U.S. Cl. .................. 514/320; 514/337; 514/422; 514/444; 514/449; 549/60; 549/473; 549/510; 549/214; 548/525; 546/196; 546/269
[58] Field of Search .................. 549/510, 60, 473, 549/214; 514/449, 320, 337, 422, 444; 546/196, 269; 548/525

[56] References Cited

U.S. PATENT DOCUMENTS

| | | | |
|---|---|---|---|
| 4,876,399 | 10/1989 | Holton et al. | 568/817 |
| 4,924,012 | 5/1990 | Colin et al. | 549/510 |
| 4,960,790 | 10/1990 | Stella et al. | 514/449 |
| 5,015,744 | 5/1991 | Holton | 549/510 |
| 5,175,315 | 12/1992 | Holton | 549/510 |
| 5,264,591 | 11/1993 | Bombardelli et al. | 549/214 |

FOREIGN PATENT DOCUMENTS

| | | |
|---|---|---|
| 0400971 | 12/1990 | European Pat. Off. . |
| WO92/09589 | 6/1992 | WIPO . |

OTHER PUBLICATIONS

Appendino et al., "14β–Hydroxy–10–deacetylbaccatin III, a New Taxane from Himalayan Yew (Taxus Wallichiana Zucc.)", *J. Chem. Soc., Perkin Trans.*, 1, 2925–2529 (1992).

Ojima et al., "New and Efficient Approaches to the Semisynthesis of Taxol and its C–13 Side Chain Analogs by Means of β–Lactam Synthon Method", *Tetrahedron*, 48, 6985–7012 (1992).

Commercon et al., "Improved Protection and Esterification of a Precursor of the Taxotère® and Taxol Side Chains", *Tetrahedron Lett.*, 33, 5185–5188 (1992).

Denis et al., "A Highly Efficient, Practical Approach to Natural Taxol", *J. Am. Chem. Soc.*, 110, 5917–5919 (1988).

Mangatal et al., "Application of the Vicinal Hydroxyamination Reaction with Asymmetric Induction to the Hemisynthesis of Taxol and Analogs", *Tetrahedron*, 45, 4177–90 (1989).

Kingston, "The Chemistry of Taxol", *Pharmac. Ther.*, 52, 1–34 (1991).

McLaughlin et al., "19–Hydroxybaccatin III, 1–deacetylcephalomannine, and 10–deacetyltaxol: new antitumor taxanes from Taxus Wallichiana", *J. Nat. Prod.*, 44, 312–319 (1981).

Riondel et al., "Antineoplastic Activity of Two Taxol Derivatives on an Ovarian Tumor Xenografted Into Nude Mice", *Anticancer Res.*, 8, 387–390 (1988).

Guèritte–Voegelein et al., "Relationships between the Structure of Taxol Analogues and their Antimitotic Activity", *J. Med. Chem.*, 34, 992 (1991).

Swindell et al., "Biologically Active Taxol Analogues with Deleted A–ring Side Chain Substituents and Variable C–2' Configurations", *J. Med. Chem.*, 34, 1176–1184 (1991).

Georg et al., "Taxol Photoaffinity Label: 7–(p–Azidobenzoyl) taxol Synthesis and Biological Evaluation", *BioMed. Chem. Lett.*, 2, 735–738 (1992).

Georg et al., "Synthesis of Biologically Active Taxol Analogues with Modified Phenylisoserine Side Chains", *J. Med. Chem.*, 35, 4230–4237 (1992).

Georg et al., "Semisynthesis and Biological Activity of Taxol Analogues: Baccatin III 13–(N–benzoyl)–(2'R, 3'S)–3'–(p–tolyl) isoserinate), Baccatin III 13–(N–toluoyl–2'R, 3'S)–3'–phenylisoserinate), Baccatin III 13–(N–benzoyl–(2'R, 3'S)–3'14 )p–trifluoromethylphenyl) isoserinate), and Baccatin III 13–(N–(p–trifluoromethylbenzoyl–(2'R, 3'S)–3'–phenylisoserinate", *BioMed. Chem. Lett.*, 2, 1751–1754 (1992).

(List continued on next page.)

*Primary Examiner*—Warren C. Ivy
*Assistant Examiner*—A. A. Owens
*Attorney, Agent, or Firm*—Hoffmann & Baron

[57] ABSTRACT

The present invention is directed to novel taxanes useful as chemotherapeutic agents or their precursors. Processes for preparing the novel taxanes include coupling reactions, in the presence of a base, of baccatin of formula (III) or (IV)

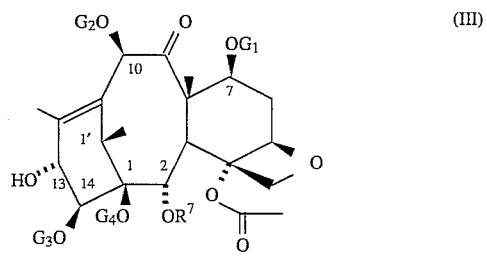

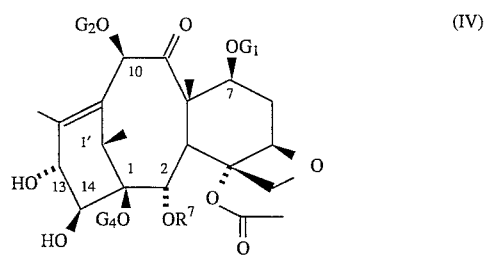

with β-lactams of formula (V).

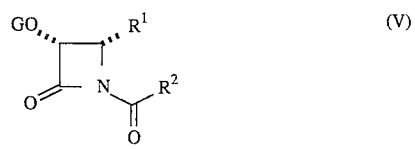

The invention also provides pharmaceutical compositions including the novel taxanes and method for treatment of certain cancers with these new compounds.

8 Claims, No Drawings

OTHER PUBLICATIONS

Matthew et al., "Synthesis and Evaluation of Some Water–Soluble Produrgs and Derivatives of Taxol with Antitumor Activity", *J. Med. Chem.*, 35, 145–151 (1992).

A. D. Seidman, "Clinical Results of Taxol in the Treatment of Advanced Breast Cancer: Single Agent Trials," *Abstracts, Stony Brook Symposium on Taxol and Taxotére*, pp. 14–16 91993).

P. M. Ravdin, "Taxotere, A Promising New Agent for the Treatment of Metastatic Breast Cancer," *Abstracts, Stony Brook symposium on Taxol and Taxotére*, p. 18 (1993).

H. Burris, et al., "Phase I Clinical Trial of Taxotere Adlinistered as either a 2–hour or 6–hour Intravenous Infusion," *J. Clin. Oncol.*, 11, pp. 950–958, (1993). Abstract.

A. Y. Chang, et al., "Phase II Study of Taxol, Merbarone, and Piroxantrone in Stage IV Non–Small–Cell Lung Cancer: The Eastern Cooperative Oncology Group Results," *J. Natl. Cancer Inst.*, 85, pp. 388–394 (1993). Abstract.

ANTI-TUMOR COMPOUNDS, PHARMACEUTICAL COMPOSITIONS, METHODS FOR PREPARATION THEREOF AND FOR TREATMENT cal trials in the United States, Europe, and Japan.

Taxol and Taxotère have chemical structures as follows:

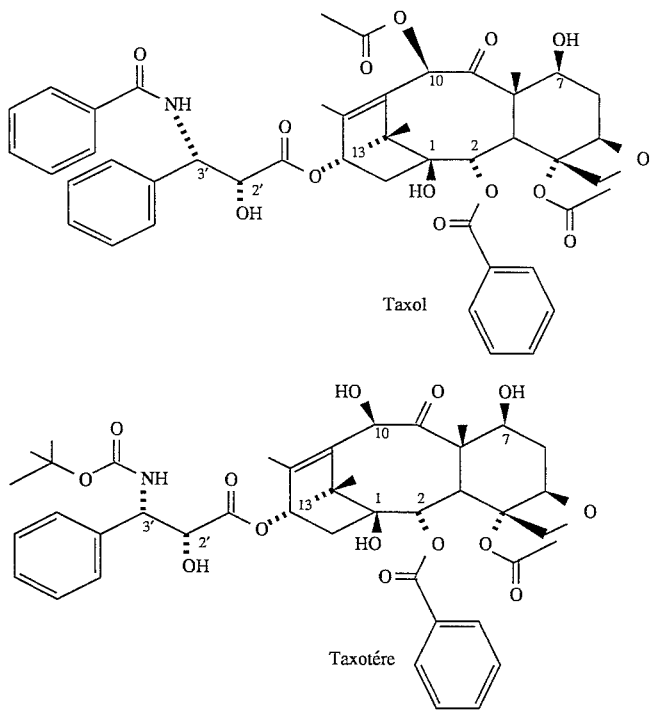

Taxol

Taxotère

This work was in part supported by a grant form the National Institute of Health (GM42798).

BACKGROUND OF THE INVENTION

The invention relates to new taxanes possessing strong antitumor activities, precursors of these compounds, compositions including these compounds, and processes for synthesizing these compounds and methods for treating tumors by using these new compounds.

Taxol is currently considered the most exciting "lead" compound in cancer chemotherapy. Taxol is a complex diterpene isolated from the bark of *Taxus Brevifolia* (Pacific Yew). Taxol possesses high cytotoxicity and strong antitumor activity against different cancers which have not been effectively treated by existing antitumor drugs. For example, taxol has been approved by FDA in late 1992 for the treatment of advanced ovarian cancer, and is currently in phase II clinical trials for breast and lung cancers.

Although Taxol is an important "lead" compound in cancer chemotherapy, Taxol has limited solubility in aqueous media, resulting in serious limitations to its use. It is also common that better drugs can be derived from naturally occurring "lead" compounds. In fact, French researchers have discovered a new anticancer agent by modifying the C-13 side chain of Taxol. This unnatural compound, named "Taxotère" has t-butoxycarbonyl instead of benzoyl on the amino group of (2R, 3S)-phenylisoserine moiety at the C-13 position and a hydroxyl group instead of acetoxy group at C-10. Taxotère has antitumor activity superior to Taxol with better bioavailability. Taxotère is currently in phase II clini- A recent report on clinical trials of Taxol and Taxotère has disclosed that Taxol has side effects such as nerve damage, muscle pain or disturbances in heart rhythm. Taxotère also has side effects. For example, Taxotère provokes mouth sores and a plunge in white blood cell count. There are other minor side effects for these two drugs.

Taxol's poor water solubility causes practical problems in its pharmaceutical applications. For example, pharmaceutical formulations containing Taxol may require special carriers. Maximum dosages in Taxol drugs are also limited by the solubility of Taxol.

Taxotère, on the other hand, has a somewhat improved water solubility and thus better pharmacological properties than Taxol, but this antitumor agent also has a solubility problem.

It has been found that 14-Hydroxy-10-deacetylbaccatin III (14-OH-DAB),

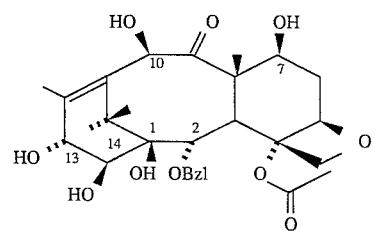

14-Hydroxy-10-deacetylbaccatin III has much higher water solubility than the usual 10-deacetylbaccatin III. 10-deacetylbaccatin III is currently used for production of Taxol and Taxotère. This higher solubility of 14-OH-DAB is due to an extra hydroxyl group at the C-14 position. Therefore, new antitumor taxanes derived from 14-OH-DAB are expected to have substantially improved water solubility and pharmacological properties as therapeutic agents. The improved pharmacological properties are believed to be related to modifications in toxicity and activity spectra against different types of cancer.

Accordingly, it is an object of the invention to develop new anti-tumor agents of the Taxol or Taxotère class which have distinct structural differences which enhance solubility.

It is a further object of the present invention to provide a series of new taxanes derived from 14-OH-DAB which possess strong antitumor activities with better therapeutic profile. It is yet another object of the present invention to synthesize the new taxanes in high yield with a minimum number of syntheses steps.

SUMMARY OF THE INVENTION

Compounds of the formula (I)

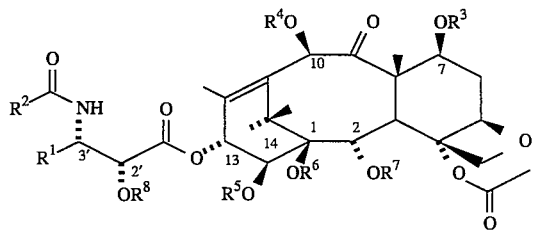

or the formula (II)

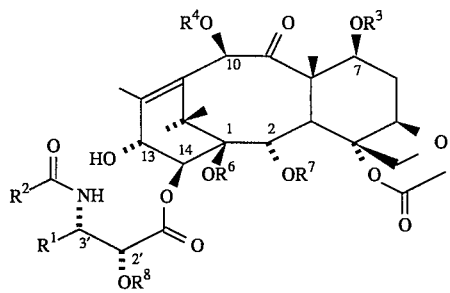

are useful as antitumor agents or their precursors.

In these compounds $R^1$ represents an unsubstituted or substituted straight chain or branched alkyl, alkenyl or alkynyl, an unsubstituted or substituted aryl or heteroaryl radical, an unsubstituted or substituted cycloalkyl, heterocycloalkyl, cycloalkenyl or heterocycloalkenyl radical;

$R^2$ is an unsubstituted or substituted straight chain or branched alkyl, alkenyl or alkynyl, cycloalkyl, heterocycloalkyl, cycloalkenyl, heterocycloalkenyl, aryl or heteroaryl;

or $R^2$ can also be an RO—, RS— or RR'N— in which R represents an unsubstituted or substituted straight chain or branched alkyl, alkenyl or alkynyl, cycloalkyl, heterocycloalkyl, cycloalkenyl, heterocycloalkenyl, aryl or heteroaryl; R' is a hydrogen or R is as defined above; R and R' can be connected to form a cyclic structure;

$R^3$ represents a hydrogen or an acyl or an alkyl or an alkenyl or an alkynyl or an unsubstituted or substituted cycloalkyl, heterocycloalkyl, cycloalkenyl or heterocycloalkenyl radical, or an unsubstituted or substituted aryl or heteroaryl radical, or a hydroxyl protecting group;

$R^4$ represents a hydrogen or an acyl radical or an alkyl, alkenyl or alkynyl radical, an unsubstituted or substituted cycloalkyl, heterocycloalkyl, cycloalkenyl or heterocycloalkenyl radical, an unsubstituted or substituted aryl or heteroaryl radical, or a hydroxyl protecting group;

$R^5$ represents a hydrogen or an acyl radical or an alkyl, alkenyl or alkynyl radical, an unsubstituted or substituted cycloalkyl, heterocycloalkyl, cycloalkenyl or heterocycloalkenyl radical, an unsubstituted or substituted aryl or heteroaryl radical, or a hydroxyl protecting group;

$R^6$ represents a hydrogen or an acyl radical or an alkyl, alkenyl or alkynyl radical, an unsubstituted or substituted cycloalkyl, heterocycloalkyl, cycloalkenyl or heterocycloalkenyl radical, an unsubstituted or substituted aryl or heteroaryl radical, or a hydroxyl protecting group;

$R^5$ and $R^6$ can be connected to form a cyclic structure;

$R^7$ represents an acyl group;

$R^8$ represents a hydrogen or a hydroxyl protecting group.

The new taxanes (I) and (II) are synthesized by processes which comprise coupling reactions, in the presence of a base, of baccatin of the formula (III)

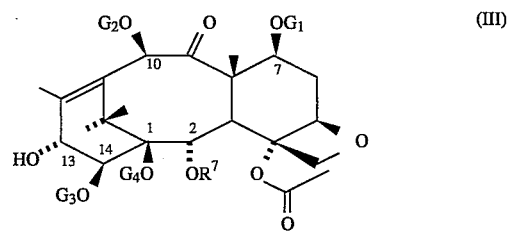

in which $G_1$, $G_2$, $G_3$ and $G_4$ represent a hydroxyl protecting group or an acyl or an alkyl or an alkenyl or an alkynyl or an unsubstituted or substituted cycloalkyl, heterocycloalkyl, cycloalkenyl or heterocycloalkenyl radical, or an unsubstituted or substituted aryl or heteroaryl radical; $G_3$ and $G_4$ can be connected to form a cyclic structure; $R^6$ has been defined above;

or of the formula (IV)

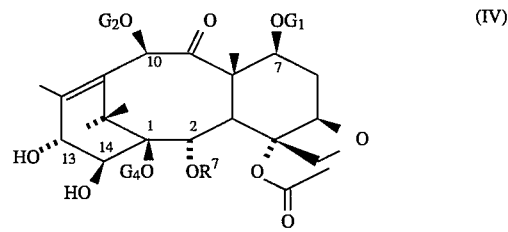

in which $G_1$, $G_2$, $G_4$, and $R^6$ have been defined above; with β-lactams of the formula (V)

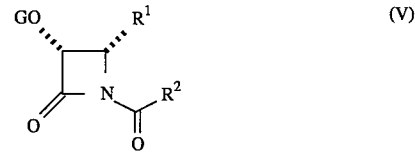

in which G is a hydroxyl protecting group such as ethoxyethyl (EE), triethylsilyl (TES) and dimethyl(tert-butyl)silyl (TBDMS), and $R^1$ and $R^2$ have been defined above.

The new taxanes of the present invention have shown strong antitumor activities against human breast, non-small cell lung, ovarian, and colon cancer cells. It is therefore very important to develop new anti-cancer drugs which have fewer undesirable side effects, better pharmacological properties, and/or activity spectra against various tumor types different from both Taxol and Taxotère.

For a better understanding of the present invention, together with other and further objects, reference is made to the following description and its scope will be pointed out in the appended claims.

DETAILED DESCRIPTION OF THE INVENTION

The new taxanes of formulae (I) or (II), as shown above, are useful as antitumor agents or their precursors. The taxanes of the present invention possess strong antitumor activities against human breast, non-small cell lung, ovarian, and colon cancer cells.

The new taxanes of the formula (I) are synthesized by modifying the baccatin of formula (III) in which

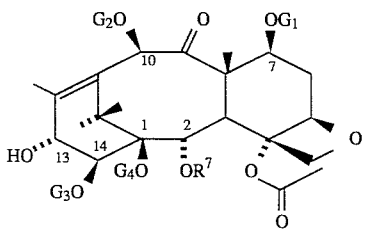

$G_1$, $G_2$, $G_3$, $G_4$, and $R^7$ have been defined above.

The new taxanes of formula (II) are synthesized by modifying the baccatin of formula (IV)

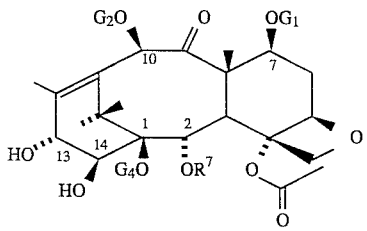

in which $G_1$, $G_2$, $G_4$, and $R^7$ have been defined above.

Precursors of (III) and (IV) are readily available. Both baccatins (III) and (IV) may be prepared by chemically modifying 14β-hydroxy-10-deacetylbaccatin (14-OH-DAB), a naturally occurring compound found in Himalayan Yew. Methods of isolations of 14-OH-DAB have been described by Appendino et al. in "14β-Hydroxy-10-deacetylbaccatin III, a New Taxane from Himalayan Yew." J. Chem. Soc. Perkin Trans I, 2525–2529 (1992), the contents of which are incorporated herein by reference.

Baccatins (III) and (IV) are coupled with β-lactams of formula (V)

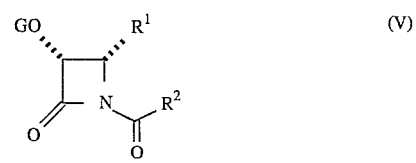

in which G, $R^1$ and $R^2$ have been defined above, to yield the new taxanes (I) and (II), respectively.

β-lactams (V) are readily prepared from β-lactams (VI) which are easily obtained through a chiral enolateimine cyclocondensation method developed in one of the inventors' laboratory as shown in Scheme 1. The cyclocondensation is described in Ojima et al., Tetrahedron, 1992, 48, 6985; Ojima, I. et al., J. Org. Chem., 56, 1681, (1991), and in U.S. patent application No. 07/842,444 filed on Feb. 27, 1992 the contents of which are incorporated herein by reference in their entirety. In this preparation, β-lactams (VI) are obtained in high yields with extremely high enantiomeric purities. Scheme 1 illustrates the synthesis of a chiral β-lactam. In Scheme 1, R* is a chiral auxiliary moiety which may be (–)-trans-2-phenyl-1-cyclohexyl, (–)- 10-dicyclohexylsulfamoyl-D-isobornyl or (–)-menthyl; TMS is a trimethylsilyl radical; the base is lithium diisopropylamide or lithium hexamethyldisilazide; and G and $R^1$ have been defined above. The removal of the 4-methoxy phenyl group from the N-position (VI') to obtain β-lactams (VI) is accomplished by treatment with cerium ammonium nitrate (CAN).

SCHEME I

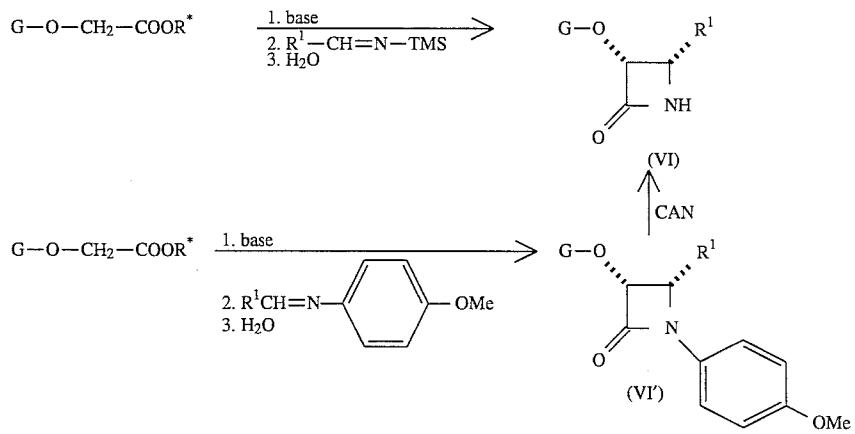

Referring now to Scheme 2, β-lactams (VIa) where G is triisopropylsilyl (TIPS) may be converted to the 3-hydroxy-β-lactams (VII), followed by protection with groups such as ethoxyethyl (EE) or triethylsilyl (TES) to give β-lactams (VI). The protecting groups can be attached to the hydroxyl group of β-lactams (VI) by methods which are generally known to those skilled in the art. β-Lactams (VI) where G is (tert-butyl)dimethylsilyl (TBDMS), may be directly obtained from the chiral enolate-imine cyclocondensation described above. β-Lactams (VI) may be reacted with acyl chlorides, chloroformates, and carbamoyl chlorides in the presence of a base to yield β-lactams (V). The β-lactams (V) may be coupled with baccatin (III) or (IV).

Scheme 3 and 4 illustrate the coupling of β-lactams (V) baccatins (III) or (IV) in the presence of a base, followed by deprotection to yield the new taxanes (I) or (II), respectively in high yields.

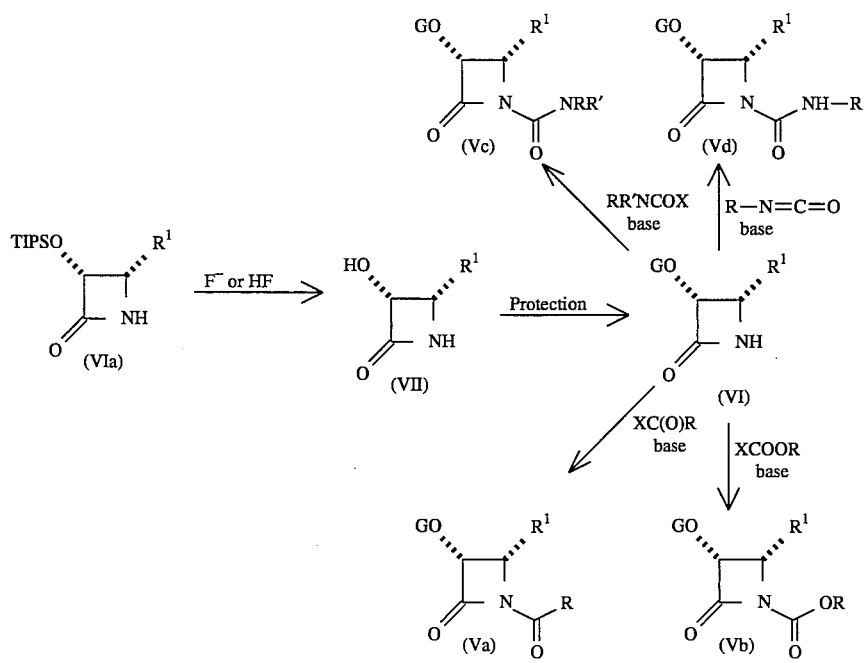

SCHEME 2

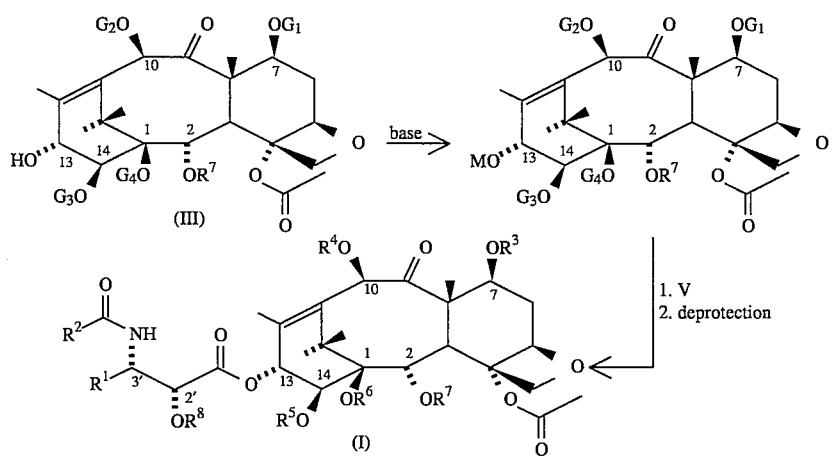

SCHEME 3

SCHEME 4

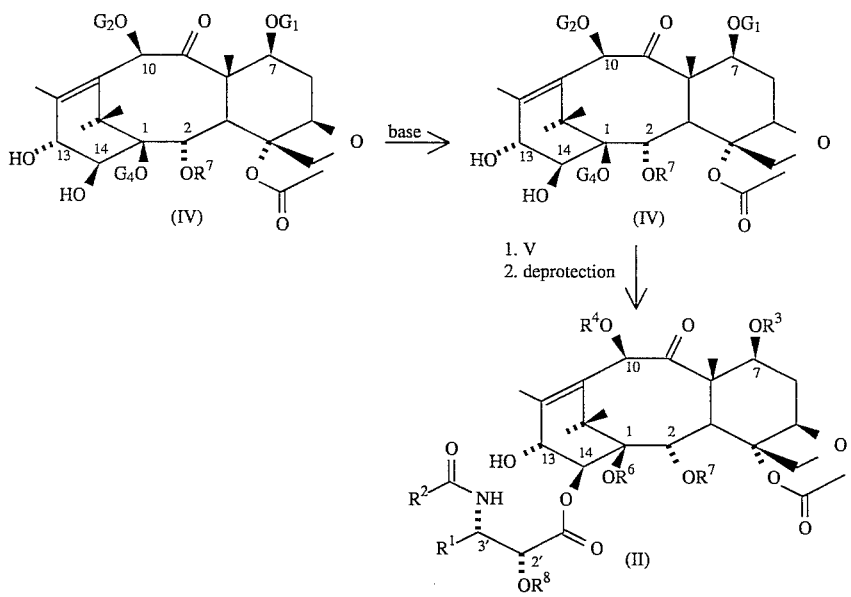

The taxanes thus obtained are represented by formulae I and II shown above. $R^1$ through $R^8$ are as generally defined above $R^1$, $R^2$ and R are each independently a straight chain or branched alkyl radical containing 1 to 10 carbon atoms, a straight chain or branched alkenyl radical containing 2 to 10 carbon atoms, or a straight chain or branched alkynyl radical containing 2 to 10 carbon atoms, a cycloalkyl radical containing 3 to 10 carbon atoms, a heterocycloalkyl radical containing 3 to 10 carbon atoms, a cycloalkenyl radical containing 3 to 10 carbon atoms, a heterocycloalkenyl radical containing 3 to 10 carbon atoms, a polycycloalkyl radical containing 6 to 20 carbon atoms, an aryl radical containing 6 to 20 carbons, a heteroaryl radical containing 3 to 15 carbon atoms; or $R^2$ can also be RO—, RS— or RR'N— radical in which R is as defined above;

R' is a hydrogen or can also be R as defined above; R and R' can be connected to form a cyclic structure which has 2 to 10 carbon atoms;

$R^3$, $R^4$, $R^5$ or $R^6$ are each independently hydrogen or an acyl radical having 1 to 20 carbons or R as defined above or a hydroxyl protecting group;

$R^7$ is an acyl group having 1 to 20 carbons;

$R^8$ is a hydrogen or a hydroxyl protecting group.

Heteroaromatic groups may also include atoms of oxygen, nitrogen and sulfur. In addition, with respect to formula (I) and (II) above, $R^3$ can also be a hydrogen or $G_1$; $R^4$ can also be a hydrogen or $G_2$; $R^5$ can also be a hydrogen or $G_3$; $R^6$ can also be a hydrogen or $G_4$; and $R^8$ can also be a hydrogen or G, in which G, $G_1$, $G_2$, $G_3$ and $G_4$ have been previously defined.

Each radical in $R^1$, $R^2$ and R as defined above can be optionally substituted with one or more halogens, hydroxyl, amino, mercapto, cyano, carboxyl group, alkoxy, alkylamino, dialkylamino, alkylthio, alkoxycarboxyl group in which said alkyl portion has 1 to 15 carbon atoms aryloxy, arylthio, aryloxycarbonyl, in which said aryl portion has 6 to 20 carbon atoms, or heteroarylthio, heteroaryloxy carbonyl in which said heteroaryl portion has 3 to 15 carbon atoms.

In one embodiment, $R^1$ can also be an alkyl radical selected from the group consisting of methyl, ethyl, propyl, isopropyl, butyl, isobutyl, tert-butyl, pentyl, isopentyl, neopentyl, hexyl, isohexyl, heptyl, isoheptyl, octyl, isooctyl, cyclohexylmethyl, cyclohexylethyl, benzyl, phenylethyl, cyclopropyl, cyclobutyl, cyclopentyl, cyclohexyl, cycloheptyl, cyclooctyl, and adamantyl, or an alkenyl radical selected from the group consisting of vinyl, allyl, 2-phenylethenyl, 2-furylethenyl, 2-pyrrolyl-ethenyl, 2-pyridylethenyl, 2-thienylethyl, or an an unsubstituted or substituted alkynyl radical selected from the group consisting of ethynyl and propargyl or an aryl radical selected from the group consisting of phenyl, tolyl, 4-methoxyphenyl, 3,4-dimethoxyphenyl, 4-fluorophenyl, 4-trifluoromethylphenyl, 4-chlorophenyl, and naphthyl; or a heteroaryl radical selected from the group consisting of furyl, pyrrolyl, and pyridyl, or a cycloalkenyl radical selected from the group consisting of cyclopentenyl, cyclohexenyl and cycloheptenyl or a heterocycloalkyl selected from the group consisting of oxiranyl, pyrrolidinyl, piperidinyl, tetrahydrofuryl, and tetrahydropyranyl, or a heterocycloalkenyl radical selected from the group consisting of dihydrofuryl, dihydropyrrolyl, dihydropiranyl, and dihydropyridyl;

$R^2$ is an unsubstituted or substituted alkyl, alkenyl, alkynyl, aryl or heteroaryl radical selected from the group consisting of phenyl, tolyl, 4-fluorophenyl, 4-chlorophenyl, 4-methoxyphenyl, biphenyl, 1-naphthyl, 2-naphthyl, isopropyl, isobutyl, neopentyl, hexyl, heptyl, cyclohexyl, cyclohexylmethyl, benzyl, phenylethyl, phenylethenyl, crotyl, allyl, vinyl, propargyl, pyridinyl, furyl, thienyl, pyrrolidinyl, and piperidinyl; or $R^2$ is RO—, RS—, or RR'N— wherein R is an unsubstituted or substituted alkyl radical selected from the group consisting of methyl, ethyl, propyl, isopropyl, butyl, isobutyl, tert-butyl, pentyl, isopentyl, neopentyl, hexyl, isohexyl, heptyl, isoheptyl, octyl, isooctyl, cyclopropyl, cyclobutyl, cyclopentyl, cyclohexyl, cycloheptyl, cyclooctyl, and adamantyl, or an alkenyl radical selected from the group consisting of vinyl and allyl, or an aryl radical selected from phenyl and naphthyl, or a heteroaryl radical selected from the group consisting of furyl, pyrrolyl, and pyridyl, or a cycloalkenyl radical selected from the group consisting of cyclopentenyl, cyclohexenyl and cycloheptenyl, or a heterocycloalkyl radical selected from the group consisting of an oxiranyl, tetrahydrofuryl, pyrrolidinyl, piperidinyl, and tetrahydropyranyl, or a heterocycloalkenyl radical selected from the group consisting of dihydrofuryl, dihydropyrrolyl, dihydropiranyl, dihydropyridyl; R' is a hydrogen or R is as defined above; cyclic RR'N— is a radical including an aziridino, azetidino, pyrrolidino, piperidino or morpholino group;

wherein said hydroxyl protecting group is selected from the group consisting of methoxymethyl, methoxyethyl, 1-ethoxyethyl, benzyloxymethyl, (β-trimethylsilylethoxy)methyl, tetrahydropyranyl, 2,2,2-trichloroethoxylcarbonyl, benzyloxycarbonyl, tert-butoxycarbonyl, 9-fluorenylmethoxycarbonyl, 2,2,2-trichloroethoxymethyl, trimethylsilyl, triethylsilyl, tripropylsilyl, dimethylethylsilyl, dimethyl(t-butyl)silyl, diethylmethylsilyl, dimethylphenylsilyl and diphenylmethylsilyl;

said acyl is selected from the group consisting of acetyl, chloroacetyl, dichloroacetyl, trichloroacetyl and trifluoroacetyl, propanoyl, butanoyl, pentanoyl, hexanoyl, heptanoyl, cyclohexanecarbonyl, octanoyl, nonanoyl, decanoyl, undecanoyl, dodecanoyl, benzoyl, phenylacetyl, nanphthalenecarbonyl, indoleacetyl, methoxycarbonyl, ethoxycarbonyl, propoxycarbonyl, and butoxycarbonyl; and $R^5$ and $R^6$ form a cyclic structure with two oxygen atoms of the skeleton of said taxane, wherein said cyclic structure is selected from the group consisting of carbonate, methylacetal, ethylacetal, propylacetal, butylacetal, phenylacetal, dimethylketal, diethylketal, dipropylketal, and dibutylketal.

In another embodiment $R^1$ may be phenyl, tolyl, 4-methoxyphenyl, 3,4-dimethoxyphenyl, 4-fluorophenyl, 4-trifluoromethyl-phenyl, 4-hydroxyphenyl, 1-naphthyl, 2naphthyl, pyridyl, furyl, thienyl, pyrrolyl, N-methylpyrrolyl, 2-phenylethenyl, 2-furylethenyl, 2-pyridylethenyl, 2-thienylethenyl, 2-phenylethyl, 2-cyclohexylethyl, cyclohexylmethyl, isobutyl or cyclohexyl;

$R^2$ is selected from the group consisting of phenyl, tolyl, 4-fluorophenyl, 4-chlorophenyl, 4-methoxyphenyl, biphenyl, 1-naphthyl, 2-naphthyl, isopropyl, isobutyl, neopentyl, hexyl, heptyl, cyclohexyl, cyclohexylmethyl, benzyl, phenylethyl, and phenylethenyl;

or $R^2$ is RO— wherein R is selected from the group consisting of a methyl, ethyl, propyl, isopropyl, butyl, isobutyl, tert-butyl, pentyl, isopentyl, neopentyl, hexyl, isohexyl, cyclohexyl, phenyl, benzyl and 9-fluorenylmethyl;

or $R^2$ is RR'N— selected from the group consisting of a methylamino, ethylamino, propylamino, isopropylamino, butylamino, isobutylamino, tert-butylamino, neopentylamino, cyclohexylamino, phenylamino or benzylamino, dimethylamino, diethylamino, dipropylamino, dibutylamino, dipentylamino, dihexylamino, dicyclohexylamino, methyl(tert-butyl)amino, cyclohexyl(methyl)amino, methyl(phenyl)amino, pyrrolidiono, piperidino, or morpholino group;

$R^3$ and $R^4$ are selected from the group consisting of a hydrogen, acetyl, chloroacetyl, dichloroacetyl, trichloroacetyl, and trifluoroacetyl, benzoyl, phenylacetyl, acryloyl, and crotyl, cinnamoyl, allyl, benzyl, methoxymethyl, methoxyethyl, 1-ethoxyethyl, tetrahydropyranyl, 2,2,2-trichloroethoxylcarbonyl, benzyloxycarbonyl, tert-butoxycarbonyl, 9-fluroenylmethoxycarbonyl, trimethylsilyl, triethylsilyl, (tert-butyl)dimethylsilyl;

$R^5$ is selected from the group consisting of a hydrogen, acetyl, chloroacetyl, allyl, benzyl, acryloyl, crotyl, and cinnamoyl and $R^6$ is a hydrogen; wherein $R^5$ and $R^6$ are connected to form a cyclic structure selected from the group consisting of carbonyl, propylidene, butylidene, pentylidene, phenylmethylidene, dimethylmethylidene, diethylmethylidene, dipropylmethylidene, dibutylmethylidene, methoxymethylidene, ethoxymethylidene, methylene, ethylene, and propylene;

$R^7$ is selected from the group consisting of benzoyl and cyclohexanecarbonyl;

$R^8$ is selected from the group consisting of a hydrogen, 1-ethoxyethyl, 2,2,2-trichloroethoxylcarbonyl, trimethylsilyl, triethylsilyl, and tert-butyldimethylsilyl.

Representative hydroxyl protecting groups include methoxylmethyl (MOM), methoxyethyl (MEM), 1-ethoxyethyl (EE), benzyloxymethyl, (β-trimethylsilylethoxy)methyl, tetrahydropyranyl, 2,2,2-trichloroethoxylcarbonyl (Troc), benzyloxycarbonyl (CBZ), tert-butoxycarbonyl (t-BOC), 9-fluorenylmethoxycarbonyl (Fmoc), 2,2,2-trichloroethoxymethyl, trimethylsilyl, triethylsilyl, tripropylsilyl, dimethylethylsilyl, dimethyl(t-butyl)silyl, diethylmethylsilyl, dimethylphenylsilyl and diphenylmethylsilyl, acetyl, chloroacetyl, dichloroacetyl, trichloroacetyl or trifluoroacetyl.

The coupling reaction of baccatin (III) or (IV) and β-lactam (V), as shown in Schemes 3 and 4, occurs at an alkali metal alkoxide which is located at the C-13 hydroxyl group of baccatin (III) or at the C-14 hydroxyl group of baccatin (IV). The alkoxide can be readily generated by reacting the baccatin with an alkali metal base.

Representative alkyl metal bases include sodium hexamethyldisilazide, potassium hexamethyldisilazide, lithium hexamethyldisilazide, sodium diisopropylamide, potassium diisopropylamide, lithium diisopropylamide, sodium hydride, in a dry nonprotic organic solvent. Tetrahydrofuran (THF), dioxane, ether, dimethoxyethane (DME), diglyme, dimethylformamide (DMF), or mixtures of these solvents with hexane, toluene, and xylene are useful nonprotic organic solvents. The coupling reaction is preferrably carried out in a temperature range from about −100° C. to about 50° C., and more preferably from about −50° C. to about 25° C.

The coupling reaction is also preferably carried out under an inert gas atmosphere such as nitrogen and argon. The amount of base used for the reaction is preferably approximately equivalent to the amount of baccatin when soluble bases such as sodium hexamethyldisilazide, potassium hexamethyldisilazide, lithium hexamethyldisilazide, sodium diisopropylamide, potassium diisopropylamide, lithium diisopropylamide are being used. The use of a slight excess of base does not adversely affect the reaction. When heterogeneous bases such as sodium hydride and potassium hydride are used, 5–10 equivalents of the base to the amount of baccatin are preferably employed.

The coupling reaction at the metal alkoxide of baccatin is typically carried out by adding a solution of β-lactam in a dry non-protic organic solvent, as described above, in a preferred temperature range from about −100° C. to 50° C., and more preferably from about −50° C. to 25° C. The mixture of reactants is stirred for 15 minutes to 24 hours and the progress and completion of the reaction may be monitored by known methods such as thin layer chromatography (TLC). When the limiting reactant is completely consumed, the reaction is quenched by addition of a cold brine solution. The crude reaction mixture is worked up using standard isolation procedures, generally known to those skilled in the art, to yield the corresponding taxane. The ratio of β-lactam to baccatin is in a range from 2:1 to 1:2. More preferably a ratio of approximately 1:1 has been formed to be more economic and efficient, but this ratio is not critical for the reaction. Work-up means any routine isolation procedure used to obtain the product from the reaction mixture.

The hydroxyl protecting groups can then be removed by using standard procedures which are generally known to those skilled in the art to give desired taxane derivatives. For example, 1-ethoxyethyl and triethylsilyl groups can be removed by adding 0.5N HCl at room temperature for 36 hours. A Troc group can be removed by adding with zinc and acetic acid in methanol at 60° C. for one hour without disturbing other functional groups or the skeleton of taxane. Another method of deprotection is treating triisopropylsilyl (TIPS) or (tert-butyl)dimethylsilyl (TBDMS) groups with fluoride ion.

The compounds of the invention can be formulated in pharmaceutical preparations or formulated in the form of pharmaceutically acceptable salts thereof, particularly as nontoxic pharmaceutically acceptable acid addition salts or acceptable basic salts. These salts can be prepared from the compounds of the invention according to conventional chemical methods.

Normally, the salts are prepared by reacting the free base or acid with stoichiometric amounts or with an excess thereof of the desired salt forming inorganic or organic acid in a suitable solvent or various combination of solvents. As an example, the free base can be dissolved in an aqueous solution of the appropriate acid and the salt recovered by standard techniques, for example, by evaporation of the solution. Alternatively, the free base can be dissolved in an organic solvent such as a lower alkanol, an ether, an alkyl ester, or mixtures thereof, for example, methanol, ethanol, ether, ethyl acetate, an ethyl acetate-ether solution, and the like, whereafter it is treated with the appropriate acid to form the corresponding salt. The salt is recovered by standard recovery techniques, for example, by filtration of the desired salt on spontaneous separation from the solution or it can be precipitated by the addition of a solvent in which the salt is insoluble and recovered therefrom.

Due to their antineoplastic activity, the taxane compounds of the invention can be utilized in the treatment of cancers. The new compounds are administrable in the form of tablets, pills, powder mixtures, capsules, injectables, solutions, suppositories, emulsions, dispersions, food premix, and in other suitable forms. The pharmaceutical preparation which contains the compound is conveniently admixed with a nontoxic pharmaceutical organic carrier, usually about 0.01 mg up to 2500 mg. or higher per dosage unit, preferably 50–500 mg. Typical of pharmaceutically acceptable carriers are, for example, manitol, urea, dextrans, lactose, potato and maize starches, magnesium stearate, talc, vegetable oils, polyalkylene glycols, ethyl cellulose, poly(vinylpyrrolidone), calcium carbonate, ethyl oleate, isopropyl myristate, benzyl benzoate, sodium carbonate, gelatin, potassium carbonate, silicic acid, and other conventionally employed acceptable carriers. The pharmaceutical preparation may also contain nontoxic auxiliary substances such as emulsifying, preserving, wetting agents, and the like as for example, sorbitan monolaurate, triethanolamine oleate, polyoxyethylene monostearate, glyceryl tripalmitate, dioctyl sodium sulfosuccinate, and the like.

The compounds of the invention can also be freeze dried and, if desired, combined with other pharmaceutically acceptable excipients to prepare formulations suitable for parenteral, injectable administration. For such administration, the formulation can be reconstituted in water (normal, saline), or a mixture of water and an organic solvent, such as propylene glycol, ethanol, and the like.

The dose administered, whether a single dose, multiple dose, or a daily dose, will, of course, vary with the particular compound of the invention employed because of the varying potency of the compound, the chosen route of administration, the size of the recipient and the nature of the patient's condition. The dosage administered is not subject to definite bounds, but it will usually be an effective amount, or the equivalent on a molar basis of the physiologically active free form produced from a dosage formulation upon the metabolic release of the active drug to achieve its desired pharmacological and physiological effects.

The following non-limiting examples are illustrative of the present invention. The full scope of the invention will be pointed out in the claims which follow the specification.

EXAMPLES

β-lactams (VI) were obtained as shown in Scheme 1 through a chiral enolate-imine cyclocondensation method in which silyloxyacetates (A) were reacted with imines or aldimines (B) and (B') in the presence of a base such as lithium diisopropylamide or lithium hexamethyldisilazide. Procedures for obtaining the starting compounds (A) and (B) or (B') are described in Examples 1–12. The materials used in Examples 1–12 in the preparation of materials (A), (B) and (B') are readily commercially available.

Example 1

Preparation of (−)-(1R, 2S)-2-phenyl-1-cyclohexyltriisopropylsilyloxyacetate (A)

A solution of (−)-(1R, 2S)-2-phenyl-1-cyclohexyl hydroxyacetate (851 mg, 3.63 mmol) was prepared through esterification of benzyloxyacetyl chloride with (−)-(1R,2S)-2-phenyl-1-cyclohexanol followed by hydrogenolysis. Then, triisopropylsilyl chloride (840 mg, 4.36 mmol) and imidazole (618 mg, 9.08 mmol) in dimethylformamide (DMF) (1.7 mL) were stirred at room temperature for 12–20 hours. The mixture was poured into pentane (25 mL), and washed with water and brine. The combined organic layers were dried over anhydrous $MgSO_4$ and concentrated in vacuo. The crude product was subjected to a purification on a short silica gel column using hexane/chloroform (3/1) as the eluant to give pure (−)-(1R, 2S)-2-phenyl-1-cyclohexyl triisopropylsilyloxyacetate (1.35 g, 95% yield) as a colorless oil.

Identification data for the above triisopropylsilyloxy-acetate are shown below:

$[\alpha]_D^{20}$−17.1° (c 3.15, $CHCl_3$); IR (neat) 1759, 1730 ('CO) $cm^{-1}$; $^1H$ NMR ($CDCl_3$) δ0.93–0.99 (m, 21H), 1.30–1.62 (m, 4H), 1.72–2.0 (m, 3H), 2.10–2.19 (m, 1H), 2.66 (dt, J =11.5, 4.0 Hz, 1H), 3.90 (d, J=16.6 Hz, 1H), 4.07 (d, J=16.6 Hz, 1H), 5.07 (dt, J=10.6, 4.0 Hz, 1H), 7.16–7.30 (m, 5H). Anal. Calcd for $C_{23}H_{38}O_3Si$: C, 70.72; H, 9.81. Found: C, 70.79; H, 9.85

Examples 2–4

Preparations of N-trimethylsilylimines (B)

N-Trimethylsilylaldimines used in the cyclo-condensation method can be readily obtained by the reaction of lithium hexamethyldisilazide with aldehydes. A typical procedure for the preparation of N-trimethylsilylbenzaldimine is described below.

In 75 mL of anhydrous THF were added 17.29 mL (75 mmol) of hexamethyldisilazane and 30 mL (75 mmol) of N-butyllithium (2.5M in hexane) at 0° C. under nitrogen. After stirring for one hour, 7.65 mL (75 mmol) of benzaldehyde was added at room temperature, and the mixture was refluxed for 3 hours. Then, 9.52 mL (75 mmol) of freshly distilled trimethylsilyl chloride was added with a syringe. The mixture was refluxed for 2 hours. A white precipitate formed during this process. The reaction mixture was then cooled to room temperature and the liquid layer was transferred with a syringe to a distillation flask under nitrogen. The solvent was evaporated in vacuo, and the oily residue was distilled under reduced pressure (68° C./1 mm Hg) to give pure N-trimethylsilylbenzaldimine as a pale yellow oil (10.6 g, 80%) having the identification data shown below:

$^1$H NMR (CDCl$_3$) δ0.18 (s, 9 H), 7.33–7.36 (m, 3H), 7.72–7.75 (m, 2H), 8.89 (s, 1H); $^{13}$C NMR (CDCl$_3$) δ–1.25, 128.34, 128.39, 131.96, 138.70, 168.32

N-trimethylsilyl(4-methoxy)benzaldimine and N-trimethylsilyl-(3,4-dimethoxy)benzaldimine were prepared in the same manner, from 4-methoxybenzaldehyde and 3,4-dimethoxy-benzaldehyde, respectively, in 78–82% yields. Identification data for the imines is set forth next to each one of these compounds.

Example 3

N-Trimethylsilyl(4-methoxy)benzaldimine

Pale yellow oil; bp 105° C./0.4 mmHg; $^1$H NMR (CDCl$_3$) δ0.00 (s, 9H), 3.60 (s, 3H), 6.69 (d, J=8.7 Hz, 2H), 7.50 (d, J=8.7 Hz, 2H), 8.66 (s, 1H).

Example 4

N-Trimethylsilyl-(3,4-dimethoxy)benzaldimine

Colorless oil; bp 140° C./0.2 mmHg; $^1$H NMR δ0.00 (s, 9H), 3.67 (s, 3H), 3.71 (s, 3H), 6.65 (d, J=8.2 Hz, 1H), 7.01 (dd, J=8.2, 1.8 Hz, 1H), 7.22 (d, J=1.8 Hz, 1H), 8.63 (s, 1H).

Examples 5–12

Preparations of N-(4-Methoxyphenyl)aldimines (B')

A typical procedure is described for the preparation of N-(4-methoxyphenyl)(4-fluoro)benzaldimine. To a solution of 4.81 g (39 mmol) of p-anisidine in 60 mL of dichloromethane was added 4.85 g (39 mmol) of 4-fluorobenzaldehyde. The mixture was stirred over anhydrous magnesium sulfate at room temperature for 15 hours. The dehydration agent was filtered off and the filtrate was concentrated in vacuo to give a crude imine. The crude imine was recrystallized from hexane/dichloro/methane to yield 7.69 g (86%) of pure N-(4-methoxyphenyl) (4-fluoro)benzaldimine as white needles.

Identification data for this imine are shown below:

Mp 99° C.; $^1$H NMR (CDCl$_3$) δ3.82 (s, 3H), 6.92 (d, J=8.7 Hz, 2H), 7.13 (t, J=8.6 Hz, 2H), 7.21 (d, J=8.7 Hz, 2H), 7.88 (dd, J=8.6, 5.7 Hz, 2H), 8.39 (s,1H).

Other N-(4-methoxylphenyl)aldimines were prepared in high yields in the same manner. Identification data for these imines are shown next to each one of these compounds.

Example 6

N-(4-Methoxyphenyl)benzaldimine

White solid; mp 71°–72° C.; $^1$H NMR (CDCl$_3$) δ3.93 (s, 3H), 6.93 (d, J=8.8 Hz, 2H), 7.23 (d, J=8.8 Hz, 2H), 7.46 (m, 3H), 7.87 (m, 2H), 8.48 (s, 1H).

Example 7

N-(4-Methoxyphenyl) (4-trifluoromethyl)benzaldimine

White needles; mp 124° C.; $^1$H NMR (CDCl$_3$) δ3.81 (s, 3H), 6.91 (d, J=8.8 Hz, 2H), 7.15 (d, J=8.8 Hz, 2H), 7.75 (d, J=8.6 Hz, 2H), 8.10 (d, J=8.6 Hz, 2H), 8.39 (s,1H).

Example 8

N-(4-Methoxyphenyl)furfuraldimine

Yellow pellets; mp 68°–70° C.; $^1$H NMR (CDCl$_3$) δ3.82 (s, 3H), 6.54 (dd, J=3.5, 1.8 Hz, 1H), 6.90 (d, J=3.5 Hz, 1H), 6.92 (d, J=8.9 Hz, 2H), 7.26 (d, J=8.9 Hz, 2H), 7.59 (d, J=1.8 Hz, 1 H), 8.31 (s, 1 H).

Example 9

N-(4-Methoxyphenyl)-3-phenylpropenaldimine

Yellow leaves; mp 119°–121° C.; $^1$H NMR (CDCl$_3$) δ3.81 (s, 3H), 6.90–7.60 (m, 7H), 8.28 (m, 1H) (ca. 1:1 mixture of stereoisomers).

Example 10

N-(4-Methoxyphenyl)-3-(2-furyl)propenaldimine

Yellow needles; mp 71°–73° C.; $^1$H NMR (CDCl$_3$) δ3.78 (s, 3H), 6.45 (dd, J=3.4, 1.6 Hz, 1H), 6.52 (d, J=3.4 Hz, 1H), 6.87 (d, J=15.8 Hz, 1H), 6.90 (d, J=8.9 Hz, 2H), 6.98 (dd, J=15.8, 8.7 Hz, 1H), 7.18 (d, J=8.9 Hz, 2H), 7.46 (d, J=1.6 Hz, 1H), 8.20 (d, J=8.7 Hz, 1H).

Example 11

N-(4-Methoxyphenyl)-3-methylbutanaldimine

Yellow oil; $^1$H NMR (CDCl$_3$) δ1.02 (d, J=6.7 Hz, 6H), 2.03 (m, 1H), 2.33 (dd, J=6.9, 5.3 Hz, 2H), 3.78 (s, 3H), 6.86 (d, J=8.8 Hz, 2H), 7.03 (d, J=8.8 Hz, 2H), 7.86 (t, J=5.3 Hz, 1H).

Example 12

N-(4-Methoxyphenyl)cyclohexylacetaldimine

Yellow oil; $^1$H NMR (CDCl$_3$) δ1.00–1.80 (m, 11H), 2.34 (dd, J=6.7, 5.4 Hz, 2H), 3.79 (s, 3H), 6.86 (d, J=8.9 Hz, 2H), 7.02 (d, J=8.9 Hz, 2H), 7.86 (t, J=5.4 Hz, 1H); IR (neat) 3033–2849, 1505, 1244, 1038, 803 cm$^{-1}$.

Chiral enolate-imine cyclocondensation reactions were run to obtain the 4-substituted-2-azetidinones (VI) and (VI') shown in Scheme 1. Other azetidinones having different substituents for R$^1$ were prepared by following the same procedures set forth in Examples 13 and 15. The identification data for these azetidinones is shown in Examples 14 and 16–20, respectively.

Examples 13–14

Preparations of (3R,4S)-3-silyloxy-4-substituted-2-azetidinones (VI)

A typical procedure is described for the preparation of (3R,4S)-3-triisopropylsilyloxy-4-phenyl-2-azetidinone (VIa). To a solution of 645 µL (4.6 mmol) of diisopropylamine in 10 mL of THF, was added 1.85 mL (4.6 mmol, 2.5M) of n-butyllithium at 0° C. The solution was stirred 1 h at 0° C. followed by the addition of 1.5 g (3.8 mmol) of (−) TIPS ester in 15 mL of THF over a 1 hour period (using a cannula) at −78° C. The reaction was stirred 2 hours at this temperature followed by the addition of 817 mg (4.6 mmol) of N-trimethylsilyl benzaldimine in 15 mL of THF over a 2 h period at −95° C. The reaction was stirred overnight at this temperature and allowed to slowly warm up at room temperature. The reaction was quenched by addition of saturated $NH_4Cl$. The aqueous layer was extracted with ether. The organic layer was washed with 3% HCl and brine, dried over $MgSO_4$ and concentrated. The crude oil was purified by chromatography on silica gel using 1:5 EtOAc/hexanes as the eluent to give 1.03 g (84%) of (3R,4S)-3-Triisopropylsilyloxy- 4-phenyl-2-azetidinone (VIa) as a white solid.

Identification data for (VIa) are shown below:

Mp 76°–77° C.; $[\alpha]_D^{20}$+52.7° (C 1.00, $CHCl_3$); $^1$H NMR (300 MHz, $CDCl_3$) δ0.86–0.93 (m, 21H), 4.81 (d, J=4.7 Hz, 1H), 5.17 (dd, J=4.7, 2.6 Hz, 1H), 6.18 (bs, 1H), 7.17–7.35 (m, 5H); $^{13}$C NMR (75 MHz, $CDCl_3$) δ11.8, 17.4, 17.5, 59.6, 79.9, 127.9, 128.0, 128.1, 136.4, 170.0; IR (KBr) 3234, 2946–2866, 1760, 1458 $cm^{-1}$. Anal. Calcd for $C_{18}H_{29}NO_2Si$: C 67.66; H 9.15; N 4.38. Found: C 67.64; H 9.25; N 4.44.

Example 14

(3R, 4S)-3-Triisopropylsilyloxy-4-(2-phenylethenyl)-2-azetidinone (VIb)

72%; colorless liquid; $^1$H NMR (300 MHz, $CDCl_3$) δ0.98–1.02 (m, 21H), 4.36 (dd, J=4.6, 8.3 Hz, 1H), 5.09 (dd, J=2.3, 4.6 Hz, 1H), 6.29 (dd, J=8.3, 16.0 Hz, 1H), 6.59 (d, J=16.0 Hz, 1H), 6.83, (bs, 1H), 7.23–7.39 (m, 5H); $^{13}$C NMR (75 MHz, $CDCl_3$) δ11.79, 17.61, 17.66, 58.34, 79.86, 126.05, 126.45, 127.90, 128.56, 134.41, 136.30, 169.69; IR (neat) 3262, 3032, 2944, 2865, 1748, 1672, 1623 $cm^{-1}$. Anal. Calcd for $C_{20}H_{31}NO_2Si$: C, 69.52; H, 9.04; N, 4.05. Found: C, 69.75; H, 9.02; N, 3.89.

Examples 15–20

Preparations of (3R,4S)-1-(4-methoxyphenyl)-3-silyloxy-4-substituted-2-azetidinones (VI')

To a solution of 2.51 mmol of diisopropylamine in 15 mL of THF was added 2.51 mL of n-butyllithium (2.5M in THF) at −10° C. After 30 min, lithium diisopropylamide (LDA) was generated and the solution was cooled to −95° C. A solution of 2.17 mmol of chiral ester in 5 mL of THF was added. After 1 hr, a solution of 2.5 mmol of the appropriate imine in 3 mL of THF was added. The mixture was stirred at −95° C. overnight, and the progress of the reaction was monitored by TLC or $^1$H NMR. The reaction was quenched with saturated $NH_4Cl$ and THF was removed using a rotary evaporator. Ether (10 mL) was added and the aqueous layer was extracted with ether (10 mL×3). Drying and removal of the solvent gave the crude product which was purified by silica gel column chromatography (hexane/ethyl acetate= 10:1) to afford the corresponding pure β-lactam. The enantiomeric excess was determined by HPLC using a CHIRAL-CEL OD column using n-hexane/isopropyl alcohol (i-PrOH) (90/10) as the eluant.

Example 15

(3R,4S)-4-(isobutyl)-1-(4-methoxyphenyl)-3-triisopropylsilyloxy- 2-azetidinone (VI'-c)

87%; pale yellow solid; mp 59°–60° C.; $[\alpha]_D^{20}$+60.46° (c 1.26, $CHCl_3$); $^1$H NMR (300 MHz, $CDCl_3$) δ0.96 (d, J=6.4 Hz, 3H), 1.03 (d, J=6.4 Hz, 3H), 1.10–1.30 (m, 21H), 1.60–1.68 (m, 1H), 1.70–1.92 (m, 2H), 3.75 (s, 3H), 4.16–4.22 (m, 1H), 5.06 (d, J=5.1 Hz, 1H), 6.86 (d, J=9.0 Hz, 2H), 7.32 (d, J=9.0 Hz, 2H); $^{13}$C NMR (75 MHz, $CDCl_3$) δ12.34, 17.82, 17.91, 22.18, 23.37, 25.34, 35.89, 55.50, 57.33, 76.34, 114.52, 118.73, 131.00, 156.29, 165.58; IR (KBr) 2946, 1742, 1513, 1458, 1249 $cm^1$. Anal. Calcd for $C_{23}H_{39}NO_3Si$: C, 68.10; H, 9.70; N, 3.45. Found: C, 68.26; H, 9.85; N, 3.35.

Example 16

(3R,4S)-4-(Cyclohexylmethyl)-1-(4-methoxyphenyl)-3-triisopropylsilyloxy-2-azetidinone (VI'-d)

83% low melting point solid; $[\alpha]_D^{20}$+43.7° (c 0.92, $CHCl_3$); $^1$H NMR (300 MHz, $CDCl_3$) δ0.85–1.95 (m, 34H), 3.78 (s, 3H), 4.19–4.25 (m, 1H), 5.05 (d, J=5.1 Hz, 1H), 6.86 (d, J=9.0 Hz, 2H), 7.32 (d, J=9.0 Hz, 2H); $^{13}$C NMR (75 MHz, $CDCl_3$) δ12.15, 17.76, 17.83, 26.12, 26.22, 26.47, 32.84, 34.22, 34.51, 55.36, 56.41, 76.13, 114.30, 118.45, 130.81, 155.99, 165.55; IR (neat) 2925–2865, 1749, 1513, 1464, 1448, 1389, 1246, 1174, 1145, 1128, 939, 882, 828, 684 $cm^{-1}$. Anal. Calcd for $C_{26}H_{43}NO_3Si$: C, 70.06; H, 9.72; N, 3.14. Found: C, 69.91; H, 9.71; N, 3.02.

Example 17

1-(4-Methoxyphenyl)-3-triisopropylsilyloxy-4-(4-fluorophenyl)-2-azetidinone (VI'-f)

White solid; mp 121°–122° C.; $[\alpha]_D^{20}$+82.5° (c 0.724, $CHCl_3$); $^1$H NMR ($CDCl_3$) δ0.82–0.84 (m, 18H), 0.86–1.01 (m, 3H), 3.62 (s, 3H), 5.02 (d, J=4.9 Hz, 1H), 5.11 (d, J= 4.9 Hz, 1H), 6.68 (d, J=6.9 Hz, 2H), 6.96–7.25 (m, 6H); IR ($CHCl_3$) 3050, 2974, 2868, 1748 $cm^{-1}$. Anal. Calcd for $C_{25}H_{34}NO_3FSi$: C, 67.69; H, 7.72; N, 3.16. Found: C, 67.77; H, 7.83; N, 3.19.

Example 18

1-(4-Methoxyphenyl)-3-triisopropylsilyloxy-4(4-trifluoromethylphenyl)-2-azetidinone (VI'-g)

White solid; mp 132°–133° C.; $[\alpha]_D^{20}$+89.7° (c 0.925, $CHCl_3$); $^1$H NMR ($CDCl_3$) δ0.87–1.15 (m, 21H), 3.74 (s, 3H), 5.21 (d, J=4.9 Hz, 1H), 5.27 (d, J=4.9 Hz, 1H), 6.79 (d, J=8.0 Hz, 2H), 7.25 (d, J=8.0 Hz, 2H), 7.46 (d, J=8.0 Hz, 2H), 7.60 (d, J=8.0 Hz, 2H); IR ($CHCl_3$) 3050, 2975, 2868, 1750, 878 $cm^{-1}$. Anal. Calcd for $C_{20}H_{34}NO_3F_3Si$: C, 63.26; H, 6.94; N, 2.84. Found: C, 63.36; H, 7.13; N, 2.88.

Example 19

1-(4-Methoxyphenyl)-3-triisopropylsilyloxy-4-(2-furyl)-2-azetidinone (VI'-h)

White solid; mp 109°–110° C.; $[\alpha]_D^{20}$ –86.2° (C 1.4, CHCl$_3$); $^1$H NMR (CDCl$_3$) δ0.98–1.10 (m, 21H), 3.75 (s, 3H), 5.20 (d, J=4.9 Hz, 1H), 5.24 (d, J=4.9 Hz, 1H), 6.35–6.40 (m, 2H), 6.81 (d, J=9.0 Hz, 2H), 7.30 (d, J=9.0 Hz, 2H), 7.42 (m, 1H); $^{13}$C NMR (CDCl$_3$) δ11.96, 17.52, 17.57, 55.43, 57.19, 78.13, 110.23, 110.63, 114.44, 118.55, 131.08, 142.80, 148.51, 156.45, 165.27. Anal. Calcd for C$_{23}$H$_{33}$NO$_4$Si: C, 66.47; H, 8.00; N, 3.37. Found: C, 66.56; H, 8.13; N, 3.30.

Example 20

1-(4-Methoxyphenyl)-3-triisopropylsilyloxy-4-{2-(2-furyl)ethenyl}-2-azetidinone (VI'-i)

White solid; mp 103.5°–105.5° C.; $[\alpha]_D$20 –128.4° (c 2.8, CHCl$_3$); $^1$H NMR (CDCl$_3$) δ1.05–1.09 (m, 21H), 3.76 (s, 3H), 4.69 (dd, J=4.9, 8.6 Hz, 1H), 5.15 (d, J=4.9 Hz, 1H), 6.25 (dd, J=8.6, 16.0 Hz, 1H), 6.29 (d, J=3.3 Hz, 1H ), 6.37 (dd, J=1.8, 3.3 Hz, 1H), 6.57 (d, J= 16.0 Hz, 1H) 6.83 (m, 2H), 7.34–7.41 (m, 3H); $^{13}$C NMR (CDCl$_3$) δ12.11, 17.70, 17.74, 55.54, 61.94, 77.18, 78.45, 107.88, 108.42, 111.26, 114.54, 118.70, 123.46, 123.82, 142.46, 190.99; IR (KBr) 2948, 2866, 1743, 1513, 1389, 1246, 1181, 1120 cm$^{-1}$. Anal. Calcd for C$_{25}$H$_{35}$NO$_4$Si: C, 67.99; H, 7.99; N, 3.17. Found: C, 68.07; H, 7.94; N, 3.10.

The transformation of β-lactam intermediates (VI') to β-lactams (VI) as shown in Scheme 1 was accomplished by methods discussed in Examples 21–23. Azetidinones obtained in this manner, (VIc) to (VIj), exemplify different R$^1$ groups. Identification data for (VIc) to (VIj) are shown next to each compound.

Examples 21–23

Transformation of N-(4-methoxyphenyl)-β-lactams (VI') to β-lactams (VI)

To a solution of 0.24 mmol of 1-(4-methoxyphenyl)-β-lactam in MeCN (20 mL) was added 0.65 mmol of cerium ammonium nitrate (CAN) in 10 mL CH$_3$CN and 20 mL of water in 20 min at –15° C. After stirring for 1 hour, it was diluted with water (20 mL), and the mixture was then extracted with ethyl acetate (15 mL×2). The combined organic layer was washed with water (7 mL), 5% Na$_2$SO$_4$ (10 mL×2), 5% Na$_2$CO$_3$(10 mL) and brine (5 mL) in sequence. Drying, removal of the solvent in vacuo followed by decolorization with activated charcoal afforded the crude product. This product was further purified by silica gel column chromatography using hexanes/ethyl acetate, 3/1 eluent to furnish N-deprotected β-lactam.

Example 21

(3R,4S)-4-(isobutyl)-3-triisopropylsilyloxy-2-azetidinone (VIc)

83%; yellow oil; $[\alpha]_D^{20}$+35.45° (c 1.33, CHCl$_3$); $^1$H NMR (300 MHz, CDCl$_3$) δ0.93 (d, J=6.6 Hz, 3H), 0.96 (d, J= 6.6 Hz, 3H), 1.05–1.25 (m, 22H), 1.52 (m, 1H), 1.67 (m, 1H), 3.78 (m, 1H), 4.96 (dd, J=4.8, 2.4 Hz, 1H), 6.02 (bs, 1H); $^{13}$C NMR (75 MHz, CDCl$_3$) δ12.12, 17.72, 17.80, 22.29, 23.08, 25.35, 39.08, 54.45, 78.04, 170.00; IR (neat) 3238, 1759, 1465, 1184 cm$^{-1}$. Anal. Calcd for C$_{16}$H$_{33}$NO$_2$Si: C, 64.16; H,11.1; N, 4.68. Found: C, 64.17; H, 10.96; N, 4.47.

Example 22

(3R,4S)-4-(Cyclohexylmethyl)-3-triisopropylsilyloxy-2-azetidinone (VId)

85%; yellow oil; $[\alpha]_D^{20}$+12.44° (c 1.46, CHCl$_3$); $^1$H NMR (300 MHz, CDCl$_3$) δ0,97–1.25 (m, 32H), 1.40–1.70 (m, 2H), 3.80 (dt, J=8.4, 4.8 Hz, 1H), 4.95 (dd, J=4.8, 2.4 Hz, 1H), 6.05 (bs, 1H); $^{13}$C NMR (75 MHz, CDCl$_3$) δ12.06, 17.77, 17.82, 26.16, 26.25, 26.46, 33.15, 33.82, 34.85, 37.72, 53.89, 77.98, 169.98; IR (neat) 3238, 1759, 1465, 1184 cm$^{-1}$. Anal. Calcd for C$_{19}$H$_{37}$NO$_2$Si: C, 67.20; H, 10.98; N, 4.12. Found: C, 67.40; H, 10.79; N, 3.98.

Example 23 preparation of (3R, 4S)-3-Triisopropylsilyloxy-4-(2-cyclohexylethyl)-2-azetidinone (VIj)

A mixture of (VIb) (100 mg, 0.29 mmol) in methanol (10 mL) and 5% Rh-C catalyst (10 mg) was hydrogenated at 50° C. and 800 psi of hydrogen for 20 hours. After the catalyst was filtered out and the solvents evaporated in vacuo, the residue was purified on a short silica gel column using hexane/ethyl acetate (5/1) as the eluant to give 95 mg (93% yield) of VIj as a colorless liquid: $[\alpha]_D^{20}$ –162.3° (c 1.46 CHCl$_3$); $^1$H NMR (CDCl$_3$) δ1.07–1.72 (m, 36H), 3.61–3.67 (m, 1H), 4.94 (dd, J=2.4, 4.8 Hz, 1H), 6.42 (bs, 1H); $^{13}$C NMR (CDCl$_3$) δ12.02, 17.79, 26.31, 26.60, 27.54, 33.19, 33.39, 33.54, 37.71, 56.44, 77.74, 170.15; IR (neat) 3236 ('NH), 2925, 2866, 1760 ('CO), 1464, 1451, 1384, 1348, 1244 cm$^{-1}$. Anal. Calcd for C$_{27}$H$_{39}$NO$_3$Si: C, 71.48; H, 8.66; N, 3.09. Found: C, 71.35; H, 8.66; N, 3.01.

The conversion of 3-TIPSO-4-substituted-2-azetidinones or β-lactams VI to β-lactams VII as shown in Scheme 2 is accomplished by methods of preparations discussed in Examples 24–28. Identification data for each β-lactam (VIIa)–(VIIe) follow each compound.

Examples 24–28

Preparation of 3-hydroxy-4-substituted-2-azetidinones (VII)

To a solution of 2.6 mmol of 3-triisopropylsilyloxy-4-substituted-2-azetidinone in 20 mL of THF, was added at room temperature. 3.1 mmol (1M in THF) of n-butyl fluoride (NBu$_4$ F). After 5 h, the solvent was evaporated and the crude oil was directly purified by chromatography on silica gel using 5:1 EtOAc/hexanes eluent to afford of 3-hydroxy-4-substituted-2-azetidinone:

Example 24

(3R,4S)-3-Hydroxy-4-phenyl-2-azetidinone (VIIa)

100%; white solid; mp 189°–190° C.; $[\alpha]_D^{20}$+181.6° (c 0.5, CH$_3$OH); $^1$H NMR (300 MHz, CD$_3$OD) δ4.84 (d, J=4.7 Hz, 1H), 5.04 (d, J=4.7 Hz, 1H), 7.25–7.35 (m, 5H); IR (KBr) 3373, 3252, 1732, 1494 cm$^{-1}$. Anal. Calcd for C$_9$H$_9$NO$_2$: C 66.25%, H 5.56%, N 8.58% Found: C 66.42% H 5.74% N 8,62%.

Example 25

(3R, 4S)-3-Hydroxy-4-(2-phenylethenyl)-2-azetidinone (VIIb)

82%; white solid; mp 143°–144° C.; $[\alpha]_D^{20}$+21.9° (c 1.05, MeOH); $^1$H NMR (300 MHz, CD$_3$OD) δ4.35 (ddd, J=0.8, 4.7, 7.7 Hz, 1H), 4.93 (d, J=4.7 Hz, 1H), 6.28 (dd, J=7.7, 16.0 Hz, 1H), 7.18–7.43 (m, 5H); $^{13}$C NMR (75 MHz, CD$_3$OD) δ58.95, 79.63, 126.83, 127.58, 128.88, 129.61, 135.28, 137.96, 172.79; IR (KBr) 3320, 3276, 1754, 1464 cm$^{-1}$. Anal. Calcd for C$_{11}$H$_{11}$NO$_2$: C, 69.83; H, 5.86; N, 7.40. Found: C, 69.72; H, 5.92; N, 7.24.

Example 26

(3R, 4S)-3-Hydroxy-4-(isobutyl)-2-azetidinone (VIIc)

94%; white solid; mp 141°–142° C; $[\alpha]_D^{20}$+26.6° (c 0.70, MeOH); $^1$H NMR (300 MHz, MeOH-d$_4$) δ0.94 (d, J=6.8 Hz 3H), 0.97 (d, J=6.8 Hz, 3H), 1.45 (m, 2H), 1.71 (sept, J=6.6 Hz, 1H), 3.75 (m, 1H), 4.79 (d, J=4.7 Hz, 1H); $^{13}$C NMR (75 MHz, MeOH-d$_4$) δ22.62, 23.48, 26.53, 39.90, 55.47, 77.76, 173.18; IR (KBr) 3274, 3178, 1762, 1685, 1155 cm$^{-1}$. Anal. Calcd for C$_7$H$_{13}$NO$_2$: C, 58.72; H, 9.15; N, 9.78. Found: C, 58.55; H, 9.41; N, 9.69.

Example 27

(3R, 4S)-4-(Cyclohexylmethyl)-3-hydroxy-2-azetidinone (VIId)

92%; white solid; mp 147°–148° C.; $[\alpha]_D^{20}$+8.73° (c, 0.573, CH$_3$OH); $^1$H NMR (300 MHz, MeOH-d$_4$) δ0.88–1.82 (m, 13H), 3.78 (m, 1H), 4.79 (d, J=4.7 Hz, 1H); $^1$H NMR (300 MHz, DMSO-d$_6$) δ0.86–1.72 (m, 13H), 3.58 (m, 1H), 4.63 (m, 1H), 5.82 (d, J=7.6 Hz, 1H), 8.13 (d, J=5.6, 1H); $^{13}$C NMR (75 MHz, MeOH-d$_4$) δ27.29, 27.41, 27.48, 34.07, 35.06, 36.11, 38.52, 55.02, 77.65, 173.22; IR (KBr) 3301, 3219, 2915, 2847, 1754, 1694, 1168 cm$^{-1}$. Anal. Calcd for C$_{10}$H$_{17}$NO$_2$: C, 65.54, H, 9.35, N, 7.64. Found: C, 65.72, H, 9.46, N, 7.42.

Example 28

3R,4S)-4-cyclohexyl-3-hydroxy-2-azetidinone (VIIe)

A suspension of 500 mg (3.06 mmol) of 4-phenyl-3-hydroxy-2-azetidinone VIa and 15 mg of Rh-C in 10 mL of methanol was heated at 90° C. under 800 psi in an autoclave. After 5 days, the hydrogen pressure was released and the catalyst filtered on celite. Evaporation of the solvent afforded a solid which was recrystallized in ethyl acetate to give 440 mg (85%) of VIIe as a white solid: White solid; mp 140°–140.5° C.; $[\alpha]_D^{20}$ +65.1° (C 0.66, CH$_3$OH); $^1$H NMR (250 MHz, MeOH-d$_4$) δ0.75–1.10 (m, 2H), 1.12–1.35 (m, 3H), 1.40–2.00 (m, 6H), 3.28 (dd, J=9.7, 4.6 Hz, 1H), 4.81 (d, J=4.6 Hz, 1H); $^1$H NMR (250 MHz, DMSO-d$_6$) δ0.75–1.00 (m, 2H), 1.10–1.35 (m, 3H), 1.37–1.55 (m, 1H), 1.58–1.85 (m, 5H), 3.10 (dd, J= 9.6, 4.7 Hz, 1H), 4.67 (m, 1H), 5.87 (d, J=7.8 Hz, 1H), 8.21 (bs, 1H); $^{13}$C NMR (63 MHz, DMSO-d$_6$) δ25.08, 25.36, 26.07, 28.83, 29.17, 37.51, 59.04, 76.41, 170.21; IR (KBr) 3312, 3219, 2928, 1726 cm$^{-1}$. Anal. Calcd for C$_9$H$_{15}$NO$_2$: C, 63.88, H, 8.93, N, 8.28. Found: C, 63.70, H, 9.00, N, 8.06.

Once formed, β-lactams (VII) required protection at the hydroxyl group. The protecting groups were attached by methods described in Examples 29–33 to yield β-lactams (VI). The identification data for β-lactams (VI) protected by different G groups are shown after each compound (VIa-EE) to (VIe-EE).

Examples 29–33

Preparation of 3-(hydroxy-protected)-4-substituted-2-azetidinones (VI)

To a solution of 1.9 mmol of 3-hydroxy-4-substituted-2-azetidinone in 20 mL of THF, was added at 0° C. 3.9 mmol of ethyl vinyl ether. After 2 hours, at 0° C. the reaction mixture was diluted with ether and washed with saturated NaHCO$_3$. The organic layer was dried over Na$_2$CO$_3$, filtered and concentrated to yield of 3-(1-ethoxyethoxy)- 4-substituted-2-azetidinone:

Example 29

(3R, 4S)-3-(1-Ethoxyethoxy)-4-phenyl-2-azetidinone (VIa-EE)

100%; white solid; mp 78°–80° C.; $^1$H NMR δ(CDCl$_3$) [0.98 (d, J=5.4 Hz), 1.05 (d, J=5.4 Hz), 3H], [1.11 (t, J=7.1 Hz), 1.12 (t, J=7.1 Hz), 3H], [3.16–3.26 (m), 3.31–3.42 (m), 3.59–3.69 (m), 2H], [4.47 (q, J=5.4 Hz), 4.68 (q, J=5.4 Hz), 1H], [4.82 (d, J=4.7 Hz), 4.85 (d, J= 4.7 Hz), 1H], 5.17–5.21 (m, 1H), 6.42 (bd, 1H), 7.35 (m, 5H); IR (KBr) 3214, 2983, 2933, 1753, 1718, 1456 cm$^{-1}$. Anal. Calcd for C$_{13}$H$_{17}$NO$_3$: C, 66.36; H, 7.28; N, 5.95. Found: C, 66.46; H, 7.11; N, 5.88.

Example 30

(3R,4S)-3-1(Ethoxyethoxy)-4-(2-phenylethenyl)-2-azetidinone(VIb-EE)

98%; white solid; mp 98°–99° C.; $^1$H NMR (300 MHz, CDCl$_3$) δ[1.17 (t, J=7.1 Hz), 1.18 (t, J=7.1 Hz), 3H], [1.26 (d, J=5.4 Hz), 1.35 (d, J=5.4 Hz), 3H], [3.44–3.52 (m), 3.60–3.68 (m), 3.75–3.82 (m), 2H], 4.41 (dd, J= 4.9, 8.5 Hz, 1H), [4.81 (q, J=5.4 Hz), 4.90 (q, J=5.4 Hz), 1H], [5.11 (d, J=4.9 Hz), 5.11 (d, J=4.9 Hz), 1H], 6.01 (bs, 1H), [6.27 (dd, J=8.5, 15.9 Hz), 6.28 (dd, J=8.5, 15.9 Hz), 1H], [6.61 (d, J=15.9 Hz), 6.63 (d, J=15.9 Hz), 1H], 7.27–7.42 (m, 5H); $^{13}$C NMR (75 MHz, CDCl$_3$) δ15.04, 20.37, 20.42, 57.22, 57.81, 61.23, 62.22, 78.77, 79.29, 99.50, 99.82, 125.56, 125.79, 126.59, 128.12, 128.65, 134.47, 134.58, 136.15, 168.59, 168.77; IR (KBr) 3310, 3030, 2963, 1770 cm$^{-1}$. Anal. Calcd for C$_{15}$H$_{19}$NO$_3$: C, 68.94; H, 7.33; N, 5.36. Found: C, 69.13; H, 7.44; N, 5.16.

Example 31

(3R,4S)-3-(1-Ethoxyethoxy)-4-(isobutyl)-2-azetidinone (VIc-EE)

100% colorless oil: $[\alpha]_D^{20}$+20.93° (c 1.72, CHCl$_3$); $^1$H NMR (300 MHz, CDCl$_3$) δ0.86 (d, J=6.5 Hz, 3H), 0.92 (d, J=6.5 Hz, 3H), 1.17 (t, J=7.0 Hz, 3H), [1.29 (d, J=5.3 Hz), 1.34 (d, J=5.3 Hz), 3H], 1.46 (m, 2H), 1.62 (m, 1H), [3.49 (m), 3.69 (m), 2H], 3.80 (m, 1H), [4.79 (q, J=5.4 Hz), 4.90 (q, J=5,4 Hz), 1H], 4.87 (m, 1H), 6.78 (bs, 1H); $^{13}$C NMR (75 MHz, CDCl$_3$) δ15.08, 20.42, (21.98, 22.06), (23.15, 23.22), 25.35, (39.01, 39.10), (53.35, 53.69), (61.24, 62.24), (77.79, 77.92), (99.75, 100.05), (169.56, 169.65); IR (neat) 3269, 2956, 2871, 1758, 1468, 1382, 1340, 1152, 1115, 1083, 1052, 936, 893 cm$^{-1}$.

Example 32

(3R,4S)-4-(Cyclohexylmethyl)-3-(1-ethoxyethoxy)-2-azetidinone (VId-EE)

100%; colorless oil; $[\alpha]_D^{20}$+10.92° (c 1.42, CHCl$_3$); $^1$H NMR (300 MHz, CDCl$_3$) δ0.84–1.71 (m, 13H), 1.16 (t, J= 7.0 Hz, 3H), [1.28 (d, J=5.3 Hz), 1.33 (d, J=5.3 Hz), 3H], 3.48 (m, 1H), [3.72 (m), 3.8 (m), 2H], [4.78 (q, J= 5.4 Hz), 4.85 (q, J=5.4 Hz), 1H], 4.82 (m, 1H), 6.76 (bs, 1H); $^{13}$C NMR (75 MHz, CDCl$_3$) δ14.37, 19.72, 25.30, 25.44, 25.63, (32.02, 32.13), (33.09, 33.17), (34.03, 34.07), (36.98, 37.07), (52.15, 52.49), (60.49, 61.52), (75.97, 76.39), (99.00, 99.35), (168.98, 169.05); IR (neat) 3278, 2924, 2852, 1758, 1448, 1382, 1150, 1114, 1086, 938, 886 cm$^{-1}$. Anal. Calcd for C$_{14}$H$_{25}$NO$_3$: C,65.85; H, 9.87; N, 5.49. Found: C, 66.03; H, 9.71; N, 5.30.

Example 33

(3R,4S)-4-Cyclohexyl-3-(1-ethoxyethoxy)-2-azetidinone (VIe-EE)

100%; white solid; mp 87°–89° C.; $[\alpha]_D^{20}$+83° (c 0.76, CH$_3$OH); $^1$H NMR δ (250 MHz, CDCl$_3$) 0.84 (m, 2H), 1.07–1.34 (m, 9H), 1.66 (m, 6H), 3.32 (m, 1H), [3.42 (q, J=7.7 Hz), 3.54 (q, J=7.7 Hz), 3.65 (q, J=7.7 Hz), 3.74 (q, J=7.7 Hz), 2H], 4.81 (m, 1H), [4.80 (m), 4.90 (q, J= 5.2 Hz), 1H], 6.92 (bs, 1H); IR (CHCl$_3$) 3412, 2989, 2931, 1760, 1443, 1155, 1114 cm$^{-1}$. Anal. Calcd for C$_{13}$H$_{27}$NO$_3$: C, 64.70; H, 9.61; N, 5.80. Found: C, 64.82; H, 9.66; N, 5.64.

Protected β-lactams (VI) in which G represents protecting groups described elsewhere in the specification were reacted with acyl chlorides, chloroformates or carbamoyl chlorides in the presence of a base according to preparation methods described in Examples 34 to 52. The resulting β-lactams obtained in Examples 34 to 52 are shown in Scheme 2. Identification data for β-lactams (Va) to (Vd) in which G represents different protecting groups are listed after each β-lactam following each example.

Example 34

Preparations of 1-acyl-3-(hydroxy-protected)-4-substituted-2-azetidinones (Va)

A typical procedure is described for the preparation of (3R,4S)-1-benzoyl-3-(ethoxylethoxy)-4-phenyl-2-azetidinone (Va-EE). To a solution of VIa-EE (460 mg, 1.9 mmol), 4(dimethylamino)pyridine DMAP (5 mg), and triethylamine (542 mL, 3.9 retool) in 20 mL of dichloromethane, was added dropwise benzoyl chloride (340 mL, 2.9 mmol) at 0° C. with stirring. The cooling bath was removed and the mixture was stirred at 25° C. for 2 h. The reaction mixture was washed with saturated aqueous NH$_4$Cl and brine, dried over anhydrous Na2CO$_3$ and concentrated in vacuo to give the oily crude product. The crude product was purified through a short silica gel column (eluant: EtOAc/hexanes= 1/5) to afford pure Va-EE (611 mg, 92%) as a colorless oil: IR (neat) 3064–2933, 1798, 1682, 1450 cm$^{-1}$; $^1$H NMR (CDCl$_3$) δ[1.04 (d, J=5.4 Hz), 1.14 (d, J=5.4 Hz)] (3H), 1.11–1.17 (m, 3H), 3.23–3.74 (m, 2H), [4.57 (q, J=5.4 Hz) , 4.76 (q, J=5.4 Hz)] (1H), 5.28 (d, J=6.2 Hz, 1H), [5.43 (d, J=6.2 Hz), 5.46 (d, J= 6.2 Hz )] (1H), 7.30–7.65 (m, 8H).

Examples 35–46

Preparations of 1-alkoxy- and 1-aryloxy-carbonyl-3-(hydroxy-protected)-4-substituted-2-azetidinones (Vb)

To a solution of 2.2 mmol of 3-(1-ethoxyethoxy)-4-substituted-2-azetidinone, 5 mg of DMAP, 4.5 mmol of triethylamine in 20 mL of dichloromethane, was added dropwise at 0° C. 3.3 mmol of alkyl chloroformate dissolved in 5 mL of dichloromethane. The reaction mixture was stirred overnight at room temperature. The organic layer was washed several times with brine, dried over Na$_2$CO$_3$ and concentrated. The crude solid was purified by chromatography on silica gel to yield N-protected β-lactam:

Example 35

(3R,4S)-1-Methoxycarbonyl-3-(1-ethoxyethoxy)-4-phenyl-2-azetidinone (Vb-a-EE)

62%; pale yellow oil; $[\alpha]_D^{20}$+98.2° (c 1.1, CHCl$_3$); $^1$H NMR (250 MHz, CDCl$_3$) δ[0.97 (d, J=5.4 Hz), 1.08 (d, J= 5.4 Hz), 3H], 1.10 (bt, J=7.3 Hz, 3H), [3.21 (dq, J=9.5, 7.1 Hz), 3.32 (q, J=7.1 Hz), 3.64 (dq, J=9.5, 7.1 Hz), 2H], [3.76 (s), 3.77 (s), 3H], [4.48 (q, J=5.4 Hz), 4.69 (q, J=5.4 Hz), 1H], [5.11 (d, J=5.9 Hz), 5.14 (d, J=5.9 Hz), 1H], 5.23 (d, J=5.9 Hz, 1H), 7.34 (m, 5H); $^{13}$C NMR (63 MHz, CDCl$_3$) δ (14.96, 15.07), (19.84, 20.69), 53.59, (60.74, 62.36), (61.14, 61.92), (76.21, 77.21), (99.16, 99.56), (127.73, 128.03, 128.31, 128.36, 128.62, 128.85), (133.41, 133.58), (149.51, 149.57), (165.21, 165.67); IR (neat) 3033, 2979, 2957, 1821, 1738, 1654, 1440, 1336, 1101 cm$^{-1}$. Anal. Calcd for C$_{15}$H$_{19}$NO$_5$: C, 61.42; H, 6.53; N, 4.78. Found: C, 61.55; H, 6.51; N, 4.90.

Example 36

(3R,4S)-1-Ethoxycarbonyl-3-(1-ethoxyethoxy)-4-phenyl-2-azetidinone (Vb-b-EE)

82%; colorless oil; $[\alpha]_D^{20}$+100.9° (c 1.08, CHCl$_3$); $^1$H NMR (250 MHz, CDCl$_3$) δ [0.95 (d, J=5.4 Hz), 1.06 (d, J=5.4 Hz), 3H], 1.08 (bt, J=7.3 Hz, 3H), [1.19 t, J=7.1 Hz), 1.20 (t, J=7.1 Hz), 3H], [3.20 (dq, J=9.4, 7.1 Hz), 3.31 (q, J=7.1 Hz), 3.32 (q, J=7.1 Hz), 3.63 (dq, J=9.4, 7.1 Hz), 2H], [4.18 (q, J=7.1 Hz), 4.19 (q, J=7.1 Hz), 2H], [4.47 (q, J=5.4 Hz), 4.67 (q, J= 5.4 Hz), 1H], [5.09 (d, J=5.8 Hz), 5.13 (d, J=5.8 Hz), 1H], 5.21 (d, J=5.8 Hz, 1H), 7.30 (m, 5H); $^{13}$C NMR (63 MHz, CDCl$_3$) δ14.14, (14.95, 15.07), (19.86, 20.05), (60.76, 62.35), 62.36, (61.14, 61.90), (76.18, 77.20), (99.17, 99.53), (127.73, 128.02, 128.25, 128.30, 128.50, 128.63), (133.59, 133.77), (148.99, 149.05), (165.33, 165.79); IR (neat) 2978, 2934, 1814, 1731, 1646, 1540, 1456, 1323, 1175, 1096 cm$^{-1}$. Anal. Calcd for C$_{16}$H$_{21}$NO$_5$: C, 62.53; H, 6.89; N, 4.56. Found: C, 62.45; H, 6.63; N, 4.83.

Example 37

(3R,4S)-1-n-Butoxycarbonyl-3-(1-ethoxyethoxy)-4-phenyl-2-azetidinone (Vb-c-EE)

83%; colorless oil; $[\alpha]_D^{20}$+70.4° (c 1.25, CHCl$_3$); $^1$H NMR (250 MHz, CDCl$_3$) δ0.79 (t, J=7.3 Hz, 3H), [0.94 (d, J=5.1 Hz), 1.07 (d, J=5.1 Hz), 3H], 1.07 (t, J=7.4 Hz, 3H), 1.20 (m, 2H), 1.51 (quint, J=6.7 Hz, 2H), [3.21 (m), 3.30 (q, J=7.1 Hz), 3.61 (m), 2H], 4.09 (m, 2H), [4.46 (q, J=5.2 Hz), 4.66 (q, J=5.2 Hz), 1H], [5.07 (d, J=5.8 Hz), 5.11 (d, J=5.8 Hz), 1H], 5.19 (d, J=5.8 Hz, 1H), 7.28 (m, 5H); $^{13}$C NMR (63 MHz, CDCl$_3$) δ13.50, (14.95, 15.29), 18.71, (19.84, 20.05), 30.42, (60.77, 62.33), (61.25, 62.02), 66.51, (76.24, 77.26), (99.17, 99.52), (127.76, 128.03, 128.22, 128.27, 128.50, 128.60), (133.61, 133.80), (148.96, 149.02), (165.40, 165.85); IR (neat) 2961, 2933, 1817, 1732, 1653, 1456, 1394, 1250, 1099 cm$^{-1}$. Anal. Calcd for C$_{18}$H$_{25}$NO$_5$: C, 64.46; H, 7.51; N, 4.18. Found: C, 64.44; H, 7.57; N, 4.24.

Example 38

(3R,4S)-1-tert-Butoxycarbonyl-3-(1-ethoxyethoxy)-4-phenyl-2-azetidinone (Vb-d-EE)

83%; white solid; mp 90°–91° C.; [α]$_D^{20}$+70.4° (c 1.25, CHCl$_3$); 1$^1$H NMR (250 MHz, CDCl$_3$) δ [0.96 (d, J=5.4 Hz), 1.08 (d, J=5.4 Hz), 3H], [1.09 (t, J=7.0 Hz), 1.10 (t, J=7.0 Hz), 3H], [1.36 (s), 1.37 (s), 9H], [3.23 (dq, J=9.5, 7.1 Hz), 3.32 (q, J=7.1 Hz), 3.65 (dq, J= 9.5, 7.1 Hz), 2H], [4.48 (q, J=5.4 Hz), 4.69 (q, J=5.4 Hz), 1H], [5.03 (d, J=5.8 Hz), 5.07 (d, J=5.8 Hz), 1H], 5.18 (d, J=5.8 Hz, 1H), 7.31 (m, 5H); $^{13}$C NMR (63 MHz, CDCl$_3$) δ (14.98, 15.08), (19.89, 20.10), 27.84, (60.74, 62.32), (61.28, 62.08), (75.91, 76.54), (99.10, 99.41), (127.76, 128.07, 128.20, 128.42, 128.85), (133.98, 134.16), 147.56, (165.61, 166.04); IR (CHCl$_3$) 3025, 2982, 2932, 1809, 1725, 1601, 1497, 1331, 1256, 1125 cm$^{-1}$. Anal. Calcd for C$_{18}$H$_{25}$NO$_5$: C, 64.46; H, 7.51; N, 4.18. Found: C, 64.50; H, 7.41; N, 4.17.

Example 39

(3R,4S)-3-(1-Ethoxyethoxy)-1-phenoxycarbonyl-4-phenyl-2-azetidinone (Vb-e-EE)

79%; white solid; mp 50°–52° C.; [α]$_D^{20}$+64.9° (C 0.94, CHCl$_3$); $^1$H NMR (250 MHz, CDCl$_3$) δ [1.00 (d, J=5.3 Hz), 1.11 (m), 3H], [1.14 (m), 3H], [3.27 (m), 3.35 (q, J=7.1 Hz), 3.70 (m), 2H], [4.54 (q, J=5.3 Hz), 4.74 (q, J =5.3 Hz), 1H], [5.25 (d, J=5.8 Hz), 5.29 (d, J=5.8 Hz), 1H], 5.34 (d, J=5.8 Hz, 1H), 7.03–7.39 (m, 10H); IR (CHCl$_3$) 3028, 2981, 2934, 1815, 1744, 1591, 1486, 1327, 1192 cm$^{-1}$. Anal. Calcd for C$_{20}$H$_{21}$NO$_5$: C, 67.59; H, 5.96; N, 3.94. Found: C, 67.33; H, 6.06; N, 3.75.

Example 40

(3R, 4S)-3-(1-Ethoxyethoxy)-4-phenyl-1-phenylmethoxycarbonyl-2-azetidinone (Vb-f-EE)

44%; white solid; mp 58°–60° C.; [α]$_D^{20}$+91.4° (c 1.16, CHCl$_3$); $^1$H NMR (250 MHz, CDCl$_3$) δ [0.97 (d, J=5.3 Hz), 1.09 (d, J=5.3 Hz), 3H], [1.10 (t, J=7.0 Hz), 1.11 (t, J=7.0 Hz), 3H], [3.23 (dq, J=9.5, 7.1 Hz), 3.33 (q, J=7.1 Hz), 3.66 (dq, J=9.5, 7.1 Hz), 2H], [4.50 (q, J=5.4 Hz), 4.70 (q, J=5.4 Hz), 1H], [5.13 (d, J=5.6 Hz), 5.15 (d, J=5.6 Hz), 1H], [5.19 (s), 5.20 (s), 2H], 5.23 (d, J=5.6 Hz, 1H), 7.21 (m, 2H), 7.26–7.37 (m, 8H); $^{13}$C NMR (63 MHz, CDCl$_3$) δ (14.99, 15.10), (19.90, 20.10), (60.83, 62.41), (61.64, 62.14), 68.01, (76.31, 77.28), (99.19, 99.53), (127.37, 127.86, 128.07, 128.16, 128.36, 128.52, 128.63, 128.85), (133.49, 133.68), 134.89, (148.72, 148.78), (165.37, 165.81); IR (CHCl$_3$) 3028, 2981, 2934, 1815, 1733, 1604, 1450, 1380, 1004 cm$^{-1}$. Anal. Calcd for C$_{12}$H$_{23}$NO$_5$: C, 68.28; H, 6.28; N, 3.79. Found: C, 68.07; H, 6.43; N, 3.72.

Example 41

(3R, 4S)-1-tert-Butoxycarbonyl-4-cyclohexyl-3-(1-ethoxyethoxy)-2-azetidinone (Vb-g-EE)

91%; colorless oil; [α]$_D^{20}$+62.5° (c 1.12, CHCl$_3$); $^1$H NMR (250 MHz, CDCl$_3$) δ1.10–1.28 (m, 6H), 1.15 (t, J=7.0 Hz, 3H), [1.27 (d, J=5.4 Hz), 1.31 (d, J=5.4 Hz), 3H], [1.45 (s), 1.46 (s), 9H], 1.63–1.70 (m, 5H), [3.43 (dq, J=9.2, 7.0 Hz), 3.62 (m), 3.75 (d, J=7.0 Hz), 3.78 (d, J=7.0 Hz), 2H], 3.85 (t, J=6.1 Hz, 1H), [4.78 (q, J=5.4 Hz), 4.88 (m), 1H], [4.85 (d, J=6.1 Hz), 4.86 (d, J=6.1 Hz), 1H]; $^{13}$C NMR (63 MHz, CDCl$_3$) δ 15.07, (20.25, 20.37), (26.05, 26.14), 26.26, (27.33, 27.95), (29.05, 29.20), (30.04, 30.23), (37.54, 37.64), (61.19, 62.53), (62.06, 62.32), (75.42, 75.85), 83.06, 100.11, 148.72, (166.70, 166.76); IR (neat) 2980, 2931, 2854, 1807, 1725, 1450, 1370, 1329, 1212, 1118 cm$^{-1}$. Anal. Calcd for C$_{18}$H$_{31}$NO$_5$: C, 63.32; H, 9.15; N, 4.10. Found: C, 63.15; H, 8.97; N, 3.96.

Example 42

(3R,4S)-1-tert-Butoxycarbonyl-3-(1-ethoxyethoxy)-4-(2-phenylethenyl)-2-azetidinone (Vb-h-EE)

86%; white solid; mp 69°–73° C.; $^1$H NMR (300 MHz, CDCl$_3$) δ [1.16 (t, J=7.1 Hz), 1.18 (t, J=7.1 Hz), 3H], [1.25 (d, J=5.4 Hz), 1.36 (d, J=5.4 Hz), 3H], 1.48 (s, 9H), [3.47 (m), 3.62 (m), 3.80 (m), 2H], 4.68 (dd, J=5.8, 8.8 Hz, 1H), [4.82 (q, J=5.4 Hz), 4.91 (q, 5.4 Hz), 1H], [5.09 (d, J=5.8 Hz), 5.11 (d, J=5.8 Hz), 1H], [6.23 (dd, J=8.8, 15.8 Hz), 6.25 (dd, J=8.8, 15.8 Hz), 1H], [6.72 (d, J=15.8 Hz), 6.73 (d, J=15.8 Hz), 1H], 7.27–7.44 (m, 5H); $^{13}$C NMR (75 MHz, CDCl$_3$) δ14.98, 20.31, 27.98, 60.24, 60.85, 61.46, 62.36, 63.58, 83.38, 99.63, 99.87, 122.45, 122.63, 126.69, 128.20, 128.61, 136.15, 136.34, 136.38, 147.74, 147.79, 165.33, 165.53; IR (KBr) 3027, 3020, 2984, 2933, 1809, 1723 cm$^{-1}$. Anal. Calcd for C$_{20}$H$_{27}$NO$_5$: C, 66.46; H, 7.53; N, 3.88 Found: C, 66.60; H, 7.50; N, 3.87.

Example 43

(3R,4S)-1-tert-Butoxycarbonyl-3-(1-ethoxyethoxy)-4-(isobutyl)-2-azetidinone (Vb-i-EE)

80%; yellow oil; [α]$_D^{20}$+77.45° (c 0.216, CHCl$_3$); $^1$H NMR (300 MHz, CDCl$_3$) δ0.89 (d, J=5.7 Hz, 6H), 1.41 (t, J=7.1 Hz, 3H), [1.25 (d, J=5.3 Hz ), 1.31 (d, J=5.3 Hz), 3H], 1.45 (s, 9H), 1.51–1.67 (m, 3H), [3.48 (dq, J=9.3, 7.1 Hz), 3.55–3.71 (m, 1H), 3.80 (dq, J=9.3, 7.1 Hz), 2H], 4.08 (q, J=6.1 Hz, 1H), [4.70 (q, J=5.3 Hz), 4.90 (q, J=5.3 Hz), 1H], 4.85 (d, J=6.1 Hz, 1H); $^{13}$C NMR (75 MHz, CDCl$_3$) δ14.95, (20.11, 20.28), (22.42, 22.59), 22.70, (24.89, 25.07), 27.83, (37.03, 37.31), (56.14, 56.38), (61.07, 62.27), (75.65, 75.92), 82.98, 99.91, 148.1, (166.1, 165.9); IR (neat) 2931, 2960, 2872, (1790, 1807), (1708, 1726), (1454, 1465), 1332, 1256, 1048, 1158, 996, 955, 857, 834, 770 cm$^{-1}$. Anal. Calcd for C$_{16}$H$_{29}$NO$_5$: C, 60.93; H, 9.27; N, 4.44. Found: C, 61.19; H, 9.41; N, 4.37.

Example 44

(3R,4S)-1-tert-Butoxycarbonyl-4-cyclohexylmethyl-3-(1-ethoxyethoxy)-2-azetidinone (Vb-j-EE)

93%; yellow oil; [α]$_D^{20}$+75.64° (c 0.78 CHCl$_3$); $^1$H NMR (300 MHz, CDCl$_3$) δ0.81–1.74 (m, 13H), 1.19 (t, J=7.1 Hz, 3H), 1.48 (s, 9H), [1.30 (d, J=5.3 Hz), 1.35 (d, J=5.3 Hz), 3H], [3.45 (dq, J=9.3, 7.1 Hz), 3.62–3.71 (m), 3.78 (dq, J=9.3, 7.1 Hz), 2H], 4.01 (m, 1H), [4.81 (q, J=5.3 Hz), 4.91 (q, J=5.3 Hz), 1H], [4.86 (d, J=6.1 Hz), 4.87 (d, J=6.1 Hz), 1H]; $^{13}$C NMR (75 MHz, CDCl$_3$) δ15.03, 20.19, 20.36, 26.10, 26.36, 27.91, (33.17, 33.31), (33.35, 33.49), (34.33, 34.58), (35.39, 35.68), (55.77, 55.99), (61.14, 62.21), (75.74, 75.90), 82.96, (99.86, 99.95), 147.96, 166.13; IR (neat) 2979, 2923, 2850, 1719, 1807, 1449, 1336, 1154 cm$^{-1}$. Anal. Calcd. for C$_{19}$H$_{33}$NO$_5$: C, 64.20; H, 9.36; N,3.94. Found: C, 64.00; H, 9.17; N, 4.02.

Examples 45–50

Preparations of 1-(N-monosubstituted-carbamoyl)-3-(hydroxy-protected)-4-substituted-2-azetidinones (Vd)

To a solution of 0.5 mmol of a 3-(1-hydroxy-protected)-4-substituted-2-azetidinone (VI) in 6 mL of tetrahydrofuran, was added dropwise at −78° C. 0.6 mmol of n-butylitheum (n-BuLi). After 5 min, 1 mmol of an isocyanate was added. The reaction mixture was stirred 30 min at −78° C. and quenched by addition of 2 mL sat. NH$_4$Cl solution. The reaction mixture was diluted with 30 mL of ether and the organic layer was washed several times with brine, dried over Na$_2$CO$_3$ and concentrated. The crude solid was purified by chromatography on silica gel to yield the corresponding N-carbamoyl β-lactam (Vd).

Example 45

(3R, 4S)-3-(1-Ethoxyethoxy)-1-phenylcarbamoyl-4-phenyl-2-azetidinone (Vd-a-EE)

66%; pale yellow solid; mp 152°–155° C.; [α]$_D^{20}$+87.8° (C 0.9, CHCl$_3$); $^1$H NMR (250 MHz, CDCl$_3$) δ [1.07 (d, J=5.4 Hz), 1.13 (d, J=5.4 Hz), 3H], 1.16 (t, J=7.1 Hz, 3H), [3.26 (dq, J=9.5, 7.1 Hz), 3.37 (q, J=7.1 Hz), 3.39 (q, J=7.1 Hz), 3.67 (dq, J=9.5, 7.1 Hz), 2H], [4.53 (q, J=5.4 Hz), 4.72 (q, J=5.4 Hz), 1H], 5.28 (m, 2H), [6.59 (bs), 6.60 (bs), 1H], 7.10–7.55 (m, 10H), 8.68 (bs, 1H; $^{13}$C NMR (63 MHz, CDCl$_3$) δ (15.04, 15.16), (19.98, 20.11), (60.99, 62.53), 61.80, (76.05, 76.66), (99.34, 99.70), (119.63, 120.69, 124.37, 127.67, 127.95, 128.40, 128.45, 128.67, 128.85, 129.04, 129.12, 130.49), 133.48, (137.03, 137.28), (147.23, 147.29), (168.12, 168.52); IR (CHCl$_3$) 3342, 3017, 2982, 2932, 1773, 1719, 1602, 1548, 1445, 1312, 1224, 1210 cm$^{-1}$. Anal. Calcd for C$_{20}$H$_{22}$N$_2$O$_4$: C, 67.78; H, 6.26; N, 7.90. Found: C, 67.92; H, 5.98; N, 8.17.

Example 46

(3R, 4S)-1-tert-Butoxycarbonyl-4-Phenyl-3-(1,1,1-trichloroethoxycarbonyl)-2-azetidinone (Vb-a-Troc)

White solid; mp 122°–124° C.; [α]$_D^{20}$+28° (c 0.5, CHCl$_3$); $^1$H NMR (250 MHz, CDCl$_3$) δ1.39 (s, 9H), 4.43 (d, J=11.7 Hz, 1H), 4.55 (d, J=11.7 Hz, 1H), 5.28 (d, J=5.5 Hz, 1H), 5.76 (d, J=5.5 Hz, 1H), 7.30 (m, 5H); $^{13}$C NMR (63 MHz, CDCl$_3$) δ27.81, 60.80, 77.03, 78.76, 84.40, 127.73, 128.58, 129.09, 131.55, 147.71, 152.17, 160.34; IR (CHCl$_3$) 3016, 2976, 1819, 1771, 1732, 1683, 1244 cm$^{-1}$. Anal. Calcd for C$_{17}$H$_{18}$Cl$_3$NO$_6$: C, 46.54; H, 4.14; N, 3.19. Found: C, 46.33; H, 4.34; N, 3.33.

Example 47

(3R,4S)-3-Acetyl-1-tert-butoxycarbonyl-4-phenyl-2-azetidinone (Vb-a-Ac)

White solid; mp 63°–64° C.; [α]$_D^{20}$+32.1° (c 0.81, CHCl$_3$); $^1$H NMR (250 MHz, CDCl$_3$) δ1.37 (s, 9H), 1.65 (s, 3H), 5.22 (d, J=5.5 Hz, 1H), 5.83 (d, J=5.5 Hz, 1H), 7.23–7.33 (m, 5H); $^3$C NMR (63 MHz, CDCl$_3$) δ19.71, 27.81, 60.84, 75.94, 84.07, 127.43, 128.31, 128.67, 132.44, 147.25, 162.39, 168.83; IR (CHCl$_3$) 3026, 2984, 1815, 1752, 1731, 1497, 1371, 1286, 1224, 1152, 1024 cm$^{-1}$. Anal. Calcd for C$_6$H$_{19}$NO$_5$: C, 62.94; H, 6.27; N, 4.59. Found: C, 63.17; H, 6.14; N, 4.52.

Example 48

(3R, 4S)-1-tert-Butylcarbamoyl-3-(1-ethoxyethoxy)-4-phenyl-2-azetidinone (Vb-b-EE)

74%; pale yellow viscous oil; [α]$_D^{20}$+144.3° (C 0.7, CHCl$_3$); $^1$H NMR (250 MHz, CDCl$_3$) δ[0.96 (d, J=5.3 Hz), 1.05 (d, J=5.3 Hz), 3H], 1.10 (t, J=7.1 Hz, 3H), [1.33 (s), 1.34 (s), 9H], [3.21 (dq, J=9.3, 7.0 Hz), 3.30 (q, J=7.0 Hz), 3.33 (q, J=7.1 Hz), 3.62 (dq, J= 9.1, 7.0 Hz), 2H], [4.46 (q, J=5.4 Hz), 4.66 (q, J= 5.4 Hz) , 1H], 5.10–5.19 (m, 2H), [6.59 (bs), 6.60 (bs), 1H], 7.23–7.36 (m, 5H); $^{13}$C NMR (63 MHz, CDCl$_3$) δ (14.86, 14.99), (19.75, 19.95), (28.81, 29.30), (60.62, 61.20), (60.80, 62.29), (75.57, 76.76), (98.91, 99.34), (127.07, 127.40, 127.70, 128.17, 128.29, 128.53), (133.71, 133.86), (148.54, 148.59 ), (167.67, 168.13); IR (CHCl$_3$) 3362, 3035, 2977, 2932, 1767, 1710, 1605, 1537, 1457, 1366, 1320, 1282, 1217, 1100 cm$^{-1}$. Anal. Calcd for C$_{18}$H$_{26}$N$_2$O$_4$: C, 64.65; H, 7.84; N, 8.38. Found: C, 64.46; H, 7.75; N, 8.39.

Example 49

(3R, 4S)-1-Benzylcarbamoyl-3-(1-ethoxyethoxy)-4-phenyl-2-azetidinone (Vb-c-EE)

50%; pale yellow viscous oil; [α]$_D^{20}$+66.2° (C .8, CHCl$_3$); $^1$H NMR (250 MHz, CDCl$_3$) δ[0.99 (d, J=5.5 Hz), 1.08 (d, J=5.5 Hz), 3H], 1.12 (m, 3H), [3.16–3.40 (m), 3.63 (m), 2H], [4.35–4.55 (m), 4.69 (q, J=5.5 Hz), 3H], 5.21 (m, 2H), [7.03 (bs), 7.05 (bs), 1H], 7.32 (m, 10H); $^{13}$C NMR (63 MHz, CDCl$_3$) δ (15.01, 15.14), (19.90, 20.11), 43.83, (60.66, 62.44), (60.75, 61.54), (75.93, 77.04), (99.16, 99.56), (127.25, 127.64, 127.69, 128.17, 127.93, 128.35, 128.55, 128.64, 128.74), (133.59, 133.76), 137.80, 150.02, (167.73, 168.19); IR (CHCl$_3$) 3379, 3090, 3033, 2980, 2930, 1773, 1707, 1604, 1536, 1455, 1319, 1270, 908 cm$^{-1}$. Anal. Calcd for C$_{21}$H$_{24}$N$_2$O$_4$: C, 68.46; H, 6.57; N, 7.60. Found: C, 68.30; H, 6.66; N, 7.51.

Example 50

(3R, 4S)-3-(1-Ethoxyethoxy)-1-ethylcarbamoyl-4-phenyl-2-azetidinone (Vd-d-EE)

63%; pale yellow oil; [α]$_D^{20}$+96.7° (0.9, CHCl$_3$); $^1$H NMR (250 MHz, CDCl$_3$) δ[0.96 (d, J=5.3 Hz), 1.04 (d, J= 5.3 Hz), 3H], 1.05–1.18 (m, 3H), [3.13–3.39 (m), 3.59 (m), 4H], [4.45 (q, J=5.3 Hz), 4.65 (q, J=5.3 Hz), 1H], 5.16 (m, 2H), [6.60 (bs), 6.62 (bs), 1H], 7.27 (m, 5H); $^{13}$C NMR (63 MHz, CDCl$_3$) δ14.98, (19.84, 29.93), 34.79, (60.56, 61.35), (60.72, 62.35), (75.91, 77.03), (99.14, 99.54), (127.28, 127.55, 127.85, 128.27, 128.40), (133.74, 133.89), (149.87, 149.93), (167.62, 168.07); IR (CHCl$_3$) 3378, 3035, 2980, 2934, 1774, 1704, 1537, 1455, 1321, 1271, 1112, 1025 cm$^{-1}$.

Examples 51–52

Preparations of 1-(N,N-disubstituted-carbamoyl)-3-(hydroxy-protected)-4-substituted-2-azetidinones (Vd)

A typical procedure is described for the preparation of (3R,4S)-(−)-1-morpholinecarbonyl-3-(1-ethoxyethoxy)-4-phenyl- 2-azetidinone (Vc-b). To a solution of 30 mg (0.13 mmol) of 3-(1-ethoxyethoxy)-4-phenyl-2-azetidinone VIa-EE in 2 mL of CH$_2$Cl$_2$, 2 mg of DMAP and 0.05 mL of triethylamine was added at room temperature. After 5 min, 22.9 mg (0.15 mmol) of morpholinecarbonyl chloride was added. The reaction mixture was stirred for 2 h at room temperature. The reaction mixture was diluted with 20 mL of CH$_2$Cl$_2$ and the organic layer was washed two times with brine, dried over Na$_2$CO$_3$ and concentrated. The crude solid product was purified by chromatography on silica gel to yield pure Vc-b: 87%; pale yellow oil; $^1$H NMR (250 MHz, CDCl$_3$) δ[0.90 (d, J=5.3 Hz), 1.01 (d, J=5.3 Hz)](3H), [1.04 (t, J=7.1 Hz), 1.18 (t, J=7.1 Hz)](3H), 3.20 (m, 4H), [3.28 (m), 3.53 (m), 3.67 (m)](2H), 3.60 (m, 4H), [4.41 (q, J=5.3 Hz), 4.63 (q, J=5.3 Hz)](1H), {5.07 (d, J=5.8 Hz), 5.08 (d, J=5.8 Hz)] (1H), [5.29 (d, J=5.8 Hz), 5.32 (d, J=5.8 Hz)] (1H), 7.23–7.27 (m, 5H).

Example 52

(3R,4S)-(−)-1-(N,N-Dimethylcarbomoyl)-3-(1-ethoxyethoxy)-4-phenyl-2-azetidinone (Vc-a)

55%; colorless liquid; $^1$H NMR (250 MHz, CDCl$_3$) δ[0.98 (d, J=5.4 Hz), 1.10 (d, J=5.4 Hz)] (3H), 1.12 (t, J=7.1 Hz), 1.13 (t, J=7.1 Hz), 3H], 3.16 (bs, 6H), [3.37 (m), 3.67 (m)] (2H), [4.47 (q, J=5.4 Hz), 4.71 (q, J=5.4 Hz)](1H), [5.11 (d, J=5.7 Hz), 5.12 (d, J=5.7 Hz)] (1H), 5.34 (t, J=5.7 Hz, 1H), 7.34 (m, 5H).

Examples 53–56 below provide methods of preparation of baccatins (III) and (IV) by using 14-OH-DAB, a natural compound, which was commercially obtained. Identification data for the baccatins (IIIa), (IIIb) (III-b) and (IVa) are shown following these examples.

Example 53

Preparation of 7,10-diTroc-14-hydroxy-10-deacetylbaccatin-III-1,14-carbonate (IIIa)

14-Hydroxy-10-deacetylbaccatin III (14-OH-DAB) (910 mg, 1.63 mmol) was dissolved in 18 mL of anhydrous pyridine. The solution was heated at 80° C. and 1 mL of trichloroethylchloroformate was added. After stirring for 5 min, another 0.4 mL of trichloroethylchloroformate was added and the mixture was stirred for 30 sec (total quantity of trichloroethylchloroformate: 1.4 mL, 2.15 g, 9.71 mmol, approximately 6 equivalents). The reaction flask was removed from the oil bath and the reaction mixture was checked by thin layer chromatography (TLC) to confirm the completion of the reaction. Then, some drops of methanol and a piece of ice were added to remove the excess chloroformate. The reaction mixture was extracted with CHCl$_3$ and the extract was washed with 0.1N hydrochloric acid and saturated brine. After drying over anhydrous MgSO$_4$ and removal of the solvent, the residue was purified by column chromatography on silica gel using EtOAc/hexanes (1:1) as the eluant to give 1.16 g (75%) of IIIa as a white solid. The identification data from IIIa is shown below: $^1$H NMR (CDCl$_3$) δ1.20 (s, 3H, H17), 1.28 (s, 3H, H16), 1.88 (s, 3H, H19), 2.08 (m, 1H, H6β), 2.18 (s, 3H, H18), 2.33, (s, 3H, 4-OAc), 2.63 (m, 1H, H6α), 3.75 (bs, 1H, H14), 3.82 (d, J=7.1 Hz, 1H, H3), 4.20 (d, J=8.4 Hz, 1H, H20β), 4.34 (d, J=8.4 Hz, 1H, H20α), 4.61 (d, J=11.8 Hz, 1H,Troc), 4.79 (s, 2H, Troc), 4.91 (d, J= 11.8 Hz, 1H, Troc), 4.97 (bs, 1H, H5), 5.01 (bs, 1H, OH), 5.01 (bs, 1H, H13), 5.59 (dd, J=7.2, 10.6 Hz, 1H, H7), 6.10 (d, J=7.1 Hz, 1H, H2), 6.25 (s, 1H, H10), 7.50 (m, 2H), 7.65 (m, 1H), 8.03 (d, 2H); $^{13}$C NMR (CDCl$_3$) δ10.80, 15.22, 21.56, 22.21, 25.63, 33.05, 41.28, 46.71, 56.44, 68.93, 71.79, 75.78, 76.00, 76.54, 77.56, 79.03, 79.91, 83.49, 84.09, 88.25, 94.10, 127.87, 129.01, 129.86, 130.92, 134.38, 144.81, 152.76, 153.12, 153.18, 164.73, 170.64, 199.97.

Example 54

Preparation of 14-Acetyl-7,10-DiTroc- 14-hydroxy DAB (IIIb)

To a solution of 594 mg (0.654 mmol) of 7,10-diTroc-14-hydroxy-10-deacetylbaccatin III (IIIa) in 30 mL of pyridine, was added 230 mL (3.27 mmol, 5 equiv.) of acetyl chloride at −10° C. The reaction mixture was stirred at −10° C. for 24 h. The reaction mixture was extracted with EtOAc and washed with 0.1N hydrochloric acid and brine The extract was dried over anhydrous MgSO$_4$ and concentrated in vacuo to give the crude product. The crude product was purified by flash column chromatography on silica gel using EtOAc/hexanes (1:1) as the eluant to give 402 mg (65%) of IIIb as a white solid having the identification data listed below: mp 225°–226° C.; $^1$H NMR (CDCl$_3$) δ1.10 (s, 3H), 1.21 (s, 3H), 1.88 (s, 3H), 2.02 (s, 3H), 2.05 (m, 1H, H6β), 2.19 (s, 3H), 2.38 (s, 3H), 2.64 (m, 1H, H6α), 2.74 (s, 1H, OH), 3.19 (bs, 1H, OH), 3.98 (d, J=7.3 Hz, 1H, H3), 4.23 (d, J=8.4 Hz, 1H, H20α), 4.30 (d, J=8.4 Hz, 1H, H20β), 4.61 (d, J=11.8 Hz, 1H, TROC), 4.72 (m, 1H, H13), 4.77 (d, J=7.1 Hz, 1H, TROC), 4.91 (d, J=11.8 Hz, 1H, TROC), 4.98 (m, 1H, H5), 5.39 (d, J=5.4 Hz, 1H, H14), 5.62 (dd, J=7.1, 10.5 Hz, 1H, H7), 5.84 (d, J=7.3 Hz, 1H, H2), 6.30 (s, 1H, H10), 7.44–7.62 (m, 3H), 8.03–8.06 (m, 2H). Anal. Calcd for C$_{37}$H$_{40}$Cl$_6$O$_{16}$: C, 46.61; H, 4.23. Found: C, 46.80; H, 4.39.

Example 55

Preparation of 14-hydroxy-2-cyclohexanecarbonyl-2-debenzoyl-10-deacetyl baccatin III (III-B)

A suspension of 14-hydroxy10-deacetylbaccatin III (500 mg, 0.899 mmol) and 5% Rh-C catalyst (50 mg) in MeOH (8 mL) and EtOAc (2 mL) was hydrogenated at 50° C. and 900 psi of hydrogen for 36 h. After the reaction mixture was cooled to room temperature, hydrogen gas was released, the catalyst filtered off, and the solvents evaporated in vacuo to give the crude product. The crude product was submitted to purification by column chromatography on silica gel using EtOAc/hexanes (1:1) as the eluant to give 498 mg (98%) of III-B as a white solid having the identification data listed below: $^1$H NMR (DMSO-d$^6$) δ0.88 (s, 6H), 1.46 (s, 3H), 1.86 (s, 3H), 2.14 (s, 3H), 1.12– 2.24 (m, 13H), 3.59 (m,2H), 3.93 (d, J=8.0 Hz, 1H), 3.99 (d, J=7.0 Hz, 1H), 4.25 (d, J=8.0

Hz, 1H), 4.36 (m, 1H), 4.39 (s, 1H), 4.76 (d, J=2.0 Hz, 1H), 4.88 (bd, J=9.1 Hz, 1H), 4.96 (d, J=7.1 Hz, 1H), 5.08 (d, J=2.0 Hz, 1H), 5.29 (d, J=7.1 Hz, 1H), 5.45 (d, J= 5.2 Hz, 1H), 6.64 (d, J=6.3 Hz, 1H); $^{13}$C NMR (DMSO-d$^6$) δ9.36, 14.51, 21.14, 22.05, 24.82, 25.04, 25.23, 26.40, 28.11, 28.44, 36.41, 42.04, 42.56, 45.78, 57.17, 70.70, 72.21, 73.22, 74.08, 74.54, 75.05, 75.39, 79.80, 83.58, 135.15, 139.11, 169.52, 174.62, 209.87.

Example 56

Preparation of 7,10-DiTroc-14-hydroxy-10-deacetyl baccatin III (IVa)

14-Hydroxy-10-deacetylbaccatin III (14-OH-DAB) (900 mg, 1.61 mmol) was dissolved in 18 mL of anhydrous pyridine. The solution was heated at 80° C. and 0.92 mL (1.42 g, 6.44 mmol, 4 equivalents) of trichloroethylchloroformate was added. After stirring for 5 min, the reaction flask was removed from the oil bath and the reaction mixture was checked by thin layer chromatography (TLC) to confirm the completion of the reaction. Then, some drops of methanol and a piece of ice were added to remove the excess chloroformate. The reaction mixture was extracted with CHCl$_3$ and the extract was washed with 0.1N hydrochloric acid and saturated brine. After drying over anhydrous MgSO$_4$ and removal of the solvent, the residue was purified by column chromatography on silica gel using EtOAc/hexanes (1:1) as the eluant to give 808 mg (55%) of IVa as a white solid: $^1$H NMR (CDCl$_3$) δ1.10 (s, 3H, H17), 1.18 (s, 3H, H16), 1.83 (s, 3H, H19), 2.02 (m, 1H, H6β), 2.14 (s, 3H, H18), 2.30 (s, 3H, 4-OAc), 2.61 (m, 1H, H6α), 3.22 (m, 1H, OH), 3.61 (s, 1H, OH), 3.66 (m, 1H, OH), 3.89 (d, J=7.1 Hz, H3), 4.01 (m, 1H, H14), 4.18 (d, J=8.4 Hz, 1H, H20β), 4.28 (d, J=8.4 Hz, 1H, H20α), 4.60 (d, J=11.9 Hz, 1H, Troc), 4.73 (m, 1H, H13), 4.77 (s, 2H, Troc), 4.83 (d, J=11.9 Hz, 1H, Troc), 4.95 (m, 1H, H5), 5.57 (dd, J=7.1, 10.6 Hz, 1H, H7), 5.79 (d, J=7.1 Hz, 1H, H2), 6.24 (s, 1H, H10), 7.40–7.60 (m, 3H), 8.02 (bd, 2H).

Examples 57–62 describe the syntheses of taxanes of the present invention by coupling of the β-lactams(V) with baccatins(III) and (IV) as prepared in previous examples. The coupling reactions took place in the presence of a base as shown in Schemes 3 and 4. In Example 57 the hydroxyl groups at C7 and C10 were protected, however, deprotection was carried out in Example 58. In Example 59 both coupling and deprotection took place for the syntheses of both taxanes Ib and Ic.

Examples 57–62

Synthesis of 7,10-diTroc-10-deacetyl-14-hydroxy-Taxol-1,14-carbonate (Ia-diTroc)

To a solution of baccatin IIIa (86.9 mg, 0.093 mmol) and N-benzoyl-β-lactam Va-a-EE (47.3 mg, 0.14 mmol) in 3.0 mL of THF, was added sodium hexamethyl disilazide (NaHMDS) 0.13 mL (1.2 eq, 0.85M soln. in THF) at –40° C. over the period of 30 min. TLC analysis of the reaction mixture revealed that baccatin IIIa was completely consumed. The reaction mixture was quenched with 10 mL saturated NH$_4$Cl solution. The reaction mixture was extracted with ether (10 mL×3), then dichloromethane (10 mL), and the combined extracts were washed with brine, dried over anhydrous sodium sulfate and concentrated to give the crude product. The crude product was purified by column chromatography using EtOAc/hexane (½) as the eluant to give 95.9 mg of 2'-EE-7,10-diTroc-10-deacetyl-14-hydroxy-Taxol-1,14-carbonate as a white solid. This compound was treated with 0.5N hydrochloric acid in THF at room temperature for 1 h. The reaction mixture was dried and purified by chromatography on silica gel using EtOAc/hexane (⅔) as the eluant to give 65.5 mg (75% overall yield) of taxane Ia-diTroc as a white solid having the identification data listed below: mp 178°–180° C.; [α]$_D^{20}$–5.9° (c 0.85, CHCl$_3$); $^1$H NMR (CDCl$_3$) δ1.30 (S, 6H, H16,H17), 1.89 (s, 3H, H19), 1.92, (s, 3H, H18), 2.08 (m, 1H, H6β), 2.56 (s, 3H, 4-OAc), 2.62 (m, 1H, H6α), 3.81 (d, J=7.4 Hz, 1H, H3), 4.09 (bs, 1H, 2'-OH), 4.24 (d, J=8.5 Hz, 1H, H20β), 4.31, (d, J=8.5 Hz, 1H, H20α), 4.60 (d, J=11.9 Hz, 1H, Troc), 4.76 (s, 2H, Troc), 4.87–4.94 (m, 4H, Troc,H5, H2', H14), 5.55 (dd, J=7.1, 10.5 Hz, 1H, H7), 5.93 (dd, J=2.8, 8.9 Hz, 1H, H3'), 6.11 (d, J=7.4 Hz, 1H, H2), 6.19 (s, 1H, H10), 6.47 (d, J=6.2 Hz, 1H, H13), 7.21 (d, J=8.9 Hz, 1H, NH), 7.31–7.64 (m, 11H), 7.75 (d, J=7.4 Hz, 2H), 8.12 (d, J=7.4 Hz, 2H); $^{13}$C NMR (CDCl$_3$) δ 10.93, 14.63, 22.39, 22.51, 25.39, 33.07, 41.64, 46.39, 54.92, 56.47, 68.88, 73.87, 74.42, 75.78, 75.88, 77.22, 77.45, 78.29, 79.61, 80.17, 83.59, 88.01, 94.02, 94.07, 126.80, 127.31, 127.73, 128.34, 128.64, 129.07 (2), 130.16, 132.04, 132.46, 133.44, 134.35, 137.53, 139.71, 151.63, 153.06 153.15, 164,79, 167.69, 171.37, 172.03, 199.33; IR (CHCl$_3$) 3038, 2951, 1820, 1761, 1737, 1667, 1479, 1379, 1250, 1220; Anal. Calcd for C$_{52}$H$_{49}$NCl$_6$O$_{19}$: C, 51.85; H, 4.10; N, 1.16. Found: C, 51.67; H, 3.86; N, 1.13.

Example 58

Synthesis of 10-deacetyl-14-hydroxy-Taxol-1,14-carbonate (Ia)

Taxane Ia-diTroc (100 mg) was treated with Zn dust (200 mg) in acetic acid at 40° C. for several hours. The reaction mixture was filtered on a glass filter and the filtrate was condensed in vacuo. The residue was redissolved in CH$_2$Cl$_2$, and Zn salt was removed by filtration to give the crude product. The crude product was recrystalized using EtOAc/hexane (3:1) to give pure taxane Ia (48 mg, 72 %) as a white powder: $^1$H NMR (CDCl$_3$) δ1.21 (s, 3H), 1.27 (s, 3H), 1.78 (s, 3H), 1.85 (m, 1H, H6β), 2.04 (s, 3H), 2.54 (s, 3H, 4-OAc), 2.56 (m, 1H, H6α), 3.80 (d, J=7.6 Hz, 1H, H3), 3.93 (d, J=4.4 Hz, 1H, 2'-OH), 4.28 (m, 4H, H20, H7, OH), 4.88 (m, 3H, H5, H14, H2'), 5.16 (s, 1H, H10), 5.93 (m, 1H, H3'), 6.07 (d, J=7.6 Hz, 1H, H2), 6.44 (d, J=5.8 Hz, 1H, H13), 7.23–7.60 (m, 12H), 7.73 (bd, 2H), 8.14 (bd, 2H); $^{13}$C NMR (CDCl$_3$) δ10.10, 14.22, 14.39, 21.11, 22.17, 22.61, 25.57, 36.67, 41.62, 45.97, 54.71, 57.86, 60.47, 69.43, 71.63, 73.82, 73.99, 74.66, 76.18, 77.27, 79.76, 80.43, 84.13, 88.37, 126.79, 127.40, 127.91, 128.28, 128.59, 129.07, 130.22, 131.98, 133.56, 134.25, 135.76, 136.22, 137.67, 151.89, 165.02, 167.67, 171.09, 172.06, 209.76.

Example 59

Synthesis of 13-[(2R,3S)-3-(tert-butoxycarbonyl) amino-2-hydroxy-3-phenylpropanoyl]-10-deacetyl-14-hydroxybaccatin-III-1,14-carbonate (Ib)

To a solution of baccatin IIIa (100 mg, 0.107 mmol) and N-t-BOC-β-lactam Vb-d-EE (52 mg, 0.155 mmol) in 3.0 mL of THF, was added NaHMDS 0.12 mL (1.1 eq, 1.0M soln. in THF) at –30° C. over the period of 10 min. TLC analysis of the reaction mixture revealed that baccatin IIIa was completely consumed. The reaction mixture was poured into a 100 mL beaker which contained 10 mL saturated NH$_4$Cl solution to quench the reaction. The reaction mixture was extracted with ether (10 mL×3), then dichloromethane (10 mL), and the combined extracts were washed with brine, dried over anhydrous sodium sulfate and concentrated to give a light yellow solid (170 mg). The crude product was purified by column chromatography on silica gel using EtOAc/hexane (1/1) as the eluant to afford taxane 13-[(2R, 3S)-3-(tert-butoxycarbonyl)amino-2-EEO- 3-phenylpropanoyl]-10-deacetyl-14-hydroxybaccatin-III- 1,14-carbonate (Ic-EE) (118 mg, 88%) as a white solid. The product was directly used for the next step to remove EE and Troc protecting groups all at once.

The crude taxane Ic-EE (157 mg) was treated with Zn dust (480 mg) in 2 mL glacial acid at room temperature for 8 hrs, then the temperature was raised to 50° C. for 4 hours. The solution was filtered, and the filtrate was poured into ice-cold saturated sodium bicarbonate solution (20 mL). The solution was extracted with dichloromethane (20 mL), the extract was dried over anhydrous $MgSO_4$, and concentrated to give a white solid, which was further purified by column chromatography on silica gel using EtOAc/hexane (2/1) as the eluant to afford taxane Ic (63 mg, 70% overall yield from the baccatin IIIa) having the identification data shown below: mp 190° C. (decomp.); $[\alpha]_D^{20}$ –22.83° (c, 0.193, $CHCl_3$); $^1H$ NMR (300 MHz, $CDCl_3$) δ1.36 (s, 9H, t-Boc), 1,77 (s, 3H, $H_{19}$), 1.82 (m, 1H, $H_{6b}$), 1.87 (S, 3H, $H_{18}$), 2.43 (bs, 3H, 4-OAc), 2.55 (m, 1H, $H_{6a}$), 3.69 (bs, 1H, OH), 3.80 (d, J= 7.5 Hz, H3), 4.20–4.30 (m, 3H, $H_{20}$, $H_5$), 4.69 (s, 1H, OH), 4.75 (d, J=6.7 Hz, $H_{14}$), 4.92 (d, J=8.5 Hz, 1H, $H_7$), 5.19 (s, 1H, $H_{10}$), 5.30 (m, 1H, $H_3$), 5.62 (d, J=8.6 Hz, 1H, $H_{2'}$), 6.01 (d, J=7.5 Hz, 1H, $H_2$), 6.45 (d, J=5.9 Hz, 1H, $H_{13}$), 7.51–7.64 (m, 8H), 8.02 (d, J=7.3 Hz); $^{13}C$ NMR (75 MHz, $CDCl_3$) δ9.97, 14.37, 21.98, 22.52, 25.69, 28.24, 29.68, 36.74, 41.67, 45.94, 57.91, 69.36, 71.65, 74.09, 74.31, 74.82, 76.09, 79.64, 80.58, 83.98, 88.09, 126.61, 128.13, 128.96, 129.93, 134.18, 135.82, 136.52, 138.00,151.87, 155.70, 164.78, 170.64, 171.89, 209.69; IR (neat) 3403, 2931, 1817(amide), 1734, 1715, 1703, 1242, 1085. Anal. Calcd for $C_4H_{51}NO_{16}$: C, 62.18; H, 6.05; N, 1.65. Found: C, 61.91; H, 6.33; N, 1.61.

Example 60

Synthesis of 14-[(2R, 3S)-3-(N-Benzoyl)amino-2-hydroxy-3-phenylpropanoyl]-10-deacetyl-14-hydroxybaccatin III (IIa)

To a solution of baccatin IVa (79.6 mg, 0.09 mmol) and N-benzoyl-β-lactam Va-a-EE (45.8 mg, 0.14 mmol) in 3.0 mL of THF, was added NaHMDS 0.13 mL (1.2 eq, 0.85M soln. in THF) at −40° C. over the period of 30 min. TLC analysis of the reaction mixture revealed that baccatin IIIa was completely consumed. The reaction mixture was quenched with 10 mL saturated $NH_4Cl$ solution. The reaction mixture was extracted with ether (10 mL×3), then dichloromethane (10 mL), and the combined extracts were washed with brine, dried over anhydrous sodium sulfate and concentrated to give the crude product. The crude product was purified by column chromatography on silica gel using EtOAc/hexanes (1:3) as the eluant to give 90.2 mg (82 %) of 14-[(2R, 3S)-3-(N-Benzoyl)amino-2-EEO-3-phenylpropanoyl]-10-deacetyl-14-hydroxy-baccatin III (IIa-EE) as a white solid. This protected taxane IIa-EE was treated with Zn in acetic acid at 60° C. for 9 h. The reaction mixture was filtered on a glass filter and the filtrate was condensed in vacuo. The residue was redissolved in $CH_2Cl_2$, and Zn salt was removed by filtration to give the crude product. This crude product was purified by column chromatography on silica gel using EtOAc/hexanes (3:1) as the eluant to give 33.7 mg (75 %) of taxane IIa as a white powder having the identification data shown below: mp 198°–202° C.; $[\alpha]_D^{20}$–13.2 (c 0.38, MeOH) ;$^1H$ NMR ($CDCl_3$) δ1.17 (s, 3H), 1.20 (s, 3H), 1.74 (s, 3H, H19), 1.84 (m, 1H, H6b), 2.14 (s, 3H, H18), 2.17 (s, 3H, 4-OAc), 2.60, (m, 1H, H6a), 3/07 (bs, 1H, 2'-OH), 4.03 (d, J=6.6 Hz, 1H, H3), 4.14 (d, J=8.4 Hz, 1H, H20), 4.27 (m, 3H, H20, H7, 10-OH), 4.55 (m, 1H, H2'), 4.99 (bd, 1H, H5), 5.07 (m, 1H, H13), 5.17 (d, J=5.8 Hz, 1H), 5.34 (s, 1H, H10), 5.65 (d, J=5.7 Hz, 1H, H14), 5.83 (bd, 2H, H2, H3'), 6.91 (d, J=9.4 Hz, 1H, NH), 7.36–7.59 (m, 11H), 7.77 (bd, 2H), 8.15 (bd, 2H); $^{13}C$ NMR ($CDCl_3$) δ9.53, 15.32, 20.66, 22.08, 26.03, 29.69, 37.06, 42.85, 46.50, 54.68, 58.00, 71.63, 72.06, 73.60, 75.03, 76.60, 77.12, 78.82, 80.31, 83.98, 127.10, 127.24, 128.25, 128.42, 128.84, 129.04, 130.62, 132.51, 133.59, 135.04, 137.89, 140.68, 166.49, 168.13, 170.86, 172.12, 211.58; IR ($CHCl_3$) n 3632, 3434, 3026, 3016, 2943, 2838, 1724, 1648; Anal. Calcd for $C_{45}H_{49}NO_{14}$: C, 65.29; H, 5.97; N, 1.69. Found: C, 65.15; H, 6.01; N, 1.79.

This example included a deprotection step to obtain taxane (IIa) as shown in Scheme 4.

Example 61

Synthesis of 7,10-diTroc-14-[(2R, 3S)-3-(tert-butoxycarbonyl)amino-2-hydroxy-3-phenylpropanoyl]-10-deacetyl-14-hydroxybaccatin III (IIb-diTroc)

To a solution of 50 mg (0.055 mmol) of baccatin IVa in 10 mL of THF, 0.06 mL (0.06 mmol) of NaHMDS was added at −40° C. over 10 min period. A solution of 25 mg (0.083 mmol) of N-t-BOC-β-lactam Vb-d-EE in THF was added at −40° C. and stirred for 1 hr. The reaction was quenched by addition of saturated $NH_4Cl$ at −40° C. The organic layer was separated and the aqueous layer was extracted with ethyl acetate. The combined organic extracts were dried over anhydrous $Na_2CO_3$ and concentrated in vacuo. The crude product was purified by column chromatography on silica gel using EtOAc/hexanes (1:3) as the eluant to give 54.2 mg (82 %) of 7,10-diTroc-14-[(2R,3S)-3-(tert-butoxycarbonyl)amino- 2-EEO-3-phenylpropanoyl]-10-deacetyl- 14-hydroxybaccatin III (IIb-diTroc-EE) as a white solid. This protected taxane IIb-diTroc-EE was treated with 0.5N HCl in THF at room temperature for 1 hr. The reaction mixture was dried over nhydrous $Na_2CO_3$ and purified by column chromatography on silica gel using ETOAc/hexanes (1:3) as the eluant to give 40.0 mg (81%) of taxane IIb-diTroc as a white powder: $^1H$ NMR ($CDCl_3$) δ 1.19 (s, 3H, H17), 1.24 (s, 3H, H16), 1.45 (s, 9H), 1.85 (s, 3H), 2.03 (m, 1H, H6b), 2.24 (s, 3H, H18), 2.37 (s, H, 4-OAc), 2.65 (m, 1H, H6a), 3/01 (d, J=5.7 Hz, 1H, OH), 4.01 (d, J=6.8 Hz, 1H, H3), 4.15 (d, J=8.4 Hz, 1H, H20), 4.32 (d, J=8.4 Hz, 1H, H20), 4.36 (d, J=5.6 Hz, 1H, NH), 4.62 (d, J=11.8 Hz, 1H), 4.79 (s, 2H), 4.92 (d, J=11.8 Hz, 1H), 4.95–5.02 (m, 3H, H2', H5, OH), 5.18 (d, J=9.5 Hz, 1H, H13), 5.34 (d, J=9.5 Hz, H, H14), 5.63 (dd, J=7.2, 10.5 Hz, 1H, H7), 5.71 (d, J =5.1 Hz, 1H, H3'), 5.84 (d, J=6.8 Hz, 1H, H2), 6.34 (s, 1H, H10), 7.29–7.60 (m, 8H), 8.12 (bd, 2H); $^{13}C$ NMR ($CDCl_3$) δ15.33, 22.25, 28.11, 28.17, 28.30, 28.45, 28.50, 33.26, 42.85, 46.82, 55.98, 56.51, 71.88, 73.05, 73.60, 76.22, 76.57, 77.61, 77.67, 77.88, 79.65, 80.01, 81.31, 83.54, 83.60, 94.21, 126.97, 128.29, 128.37, 128.74, 128.92 130.48, 131.21, 133.67, 138.55, 144.71, 153.07, 153.22 156.23, 166.22, 171.04, 171.97, 200.88;

This example shows only the coupling of baccatin(IVa) with β-lactams(Vb-d) protected with EE to obtain a protected taxane as shwon in Scheme 4. In this example the taxane which was obtained was IIb-diTroc.

Example 62

Synthesis of 14-[(2R,3S)-3-(tert-butoxycarbonyl) amino-2-hydroxy-3-Phenylpropanoyl]-10-deacetyl-14-hydroxybaccatin III (IIb)

To a solution of 108 mg (0.09 mmol) of IIb-diTroc in 2 mL of acetic acid and 3 mL of MeOH, 240 mg of Zn (activated) was added at room temperature. The temperature was increased to 60° C. and the mixture was stirred for 2 hrs. The reaction mixture was filtered on a glass filter and the filtrate was condensed in vacuo. The residue was redissolved in $CH_2Cl_2$, and Zn salt was removed by filtration to give 116 mg of crude product. This crude product was purified by column chromatography on silica gel using EtOAc/hexanes (4:1) as the eluant to give 48.8 mg (70 %) of taxane IIb as a white powder: $^1$H NMR ($CDCl_3$) δ1.15 (s, 3H), 1.16 (s, 3H), 1.45 (s, 9H), 1.73 (s, 3H), 1.81 (m, 1H, H6b), 2.13 (s, 3H), 2.36 (s, 3H), 2.60 (m, 1H, H6a), 3/03 (d, J=5.7 Hz, 1H, OH), 4.02 (d, J=6.9 Hz, 1H, H3), 4.17 (d, J=8.5 Hz, 1H, H20), 4.25–4.34 (m, 4H, H20, H7), 4.83 (d, J=6.0 Hz, 1H), 4.99 (m, 2H, H2', H5), 5.18 (d, J=9.5 Hz, 1H, H13), 5.31 (s, 1H, H10), 5.37 (d, J=9.5 Hz, 1H, H14), 5.67 (d, J=6.0 Hz, 1H, H3'), 5.83 (d, J=6.9 Hz, 1H, H2), 7.31–7.56 (m, 8H), 8.12 (bd, 2H);

This example illustrates the deprotection step of IIb-diTroc to obtain the taxane IIb as shown in Scheme 4.

The procedures set forth above describe highly sophisticated and elegant protocols for production of significantly enhanced compounds useful in the treatment of cancer.

Thus, while there have been described what are presently believed to be the preferred embodiments of the present invention, those skilled in the art will realize that other and further modifications can be made to the invention without departing from the true spirit of the invention, such further and other modifications are intended to be included herein within the scope of the appended claims.

We claim:

1. A compound of the formula (I)

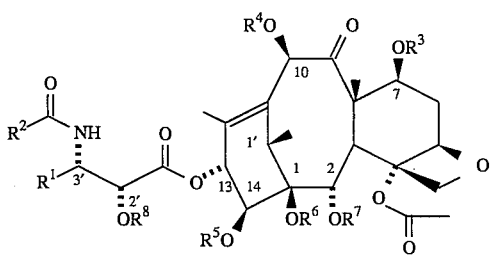

wherein $R^1$ is an unsubstituted or substituted straight chain or branched alkyl, alkenyl or alkynyl radical, an unsubstituted or substituted aryl or heteroaryl radical, an unsubstituted or substituted cycloalkyl, heterocycloalkyl, cycloalkenyl or heterocycloalkenyl radical;

$R^2$ is an unsubstituted or substituted straight chain or branched alkyl, alkenyl or alkynyl, cycloalkyl, heterocycloalkyl, cycloalkenyl, heterocycloalkenyl, aryl or heteroaryl radical;

or $R^2$ is an RO—, RS— or RR'N— wherein R is an unsubstituted or substituted straight chain or branched alkyl, alkenyl or alkynyl, cycloalkyl, heterocycloalkyl, cycloalkenyl, heterocycloalkenyl, aryl or heteroaryl radical; R' is a hydrogen or R as defined above; R and R' can be connected to form a cyclic structure;

$R^3$ is a hydrogen or an acyl or an alkyl or an alkenyl or an alkynyl or an unsubstituted or substituted cycloalkyl, heterocycloalkyl, cycloalkenyl or heterocycloalkenyl radical, or an unsubstituted or substituted aryl or heteroaryl radical or a hydroxyl protecting group;

$R^4$ is a hydrogen or an acyl radical or an alkyl, alkenyl or alkynyl radical, an unsubstituted or substituted cycloalkyl, heterocycloalkyl, cycloalkenyl or heterocycloalkenyl radical, an unsubstituted or substituted aryl or heteroaryl radical, or a hydroxyl protecting group;

$R^5$ is a hydrogen or an acyl radical or an alkyl, alkenyl or alkynyl radical, an unsubstituted or substituted cycloalkyl, heterocycloalkyl, cycloalkenyl or heterocycloalkenyl radical, an unsubstituted or substituted aryl or heteroaryl radical, or a hydroxyl protecting group;

$R^6$ is a hydrogen or an acyl radical or an alkyl, alkenyl or alkynyl radical, an unsubstituted or substituted cycloalkyl, heterocycloalkyl, cycloalkenyl or heterocycloalkenyl radical, an unsubstituted or substituted aryl or heteroaryl radical, or a hydroxyl protecting group;

$R^5$ and $R^6$ can be connected to form a cyclic structure;

$R^7$ is an acyl group;

$R^8$ is an hydrogen or a hydroxyl protecting group;

wherein, whenever $R^1$ is a phenyl radical, said phenyl radical is substituted with at least one halogen, hydroxyl, amino, mercapto, cyano, carboxyl group; alkoxy, alkylamino, dialkylamino, alkylthio, alkoxycarboxyl group wherein said alkyl portion has 1 to 15 carbon atoms; aryloxy, arylthio, aryloxycarbonyl, wherein said aryl portion has 6 to 20 carbon atoms; or heteroarylthio, heteroaryloxy carbonyl wherein said heteroaryl portion has 3 to 15 carbon atoms.

2. A compound of the formula (I)

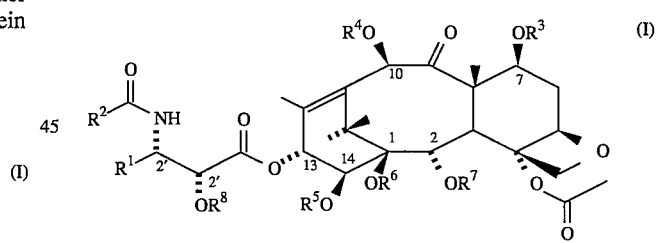

wherein $R^1$ is an unsubstituted or substituted straight chain or branched alkyl, alkenyl or alkynyl radical, an unsubstituted or substituted aryl or heteroaryl radical, an unsubstituted or substituted cycloalkyl, heterocycloalkyl, cycloalkenyl or heterocycloalkenyl radical;

$R^2$ is an unsubstituted or substituted straight chain or branched alkyl, alkenyl or alkynyl, cycloalkyl, heterocycloalkyl, cycloalkenyl, heterocycloalkenyl, aryl or heteroaryl radical;

or $R^2$ is an RO—, RS— or RR'N— wherein R is an unsubstituted or substituted straight chain or branched alkyl, alkenyl or alkynyl, cycloalkyl, heterocycloalkyl, cycloalkenyl, heterocycloalkenyl, aryl or heteroaryl radical; R' is a hydrogen or R as defined above; R and R' can be connected to form a cyclic structure;

$R^3$ is a hydrogen or an acyl or an alkyl or an alkenyl or an alkynyl or an unsubstituted or substituted cycloalkyl, heterocycloalkyl, cycloalkenyl or heterocycloalkenyl radical, or an unsubstituted or substituted aryl or heteroaryl radical or a hydroxyl protecting group;

$R^4$ is a hydrogen or an acyl radical or an alkyl, alkenyl or alkynyl radical, an unsubstituted or substituted cycloalkyl, heterocycloalkyl, cycloalkenyl or heterocycloalkenyl radical, an unsubstituted or substituted aryl or heteroaryl radical, or a hydroxyl protecting group;

$R^5$ is a hydrogen or an acyl radical or an alkyl, alkenyl or alkynyl radical, an unsubstituted or substituted cycloalkyl, heterocycloalkyl, cycloalkenyl or heterocycloalkenyl radical, an unsubstituted or substituted aryl or heteroaryl radical, or a hydroxyl protecting group;

$R^6$ is a hydrogen or an acyl radical or an alkyl, alkenyl or alkynyl radical, an unsubstituted or substituted cycloalkyl, heterocycloalkyl, cycloalkenyl or heterocycloalkenyl radical, an unsubstituted or substituted aryl or heteroaryl radical, or a hydroxyl protecting group;

$R^5$ and $R^6$ can be connected to form a cyclic structure;

$R^7$ is an acyl group;

$R^8$ is an hydrogen or a hydroxyl protecting group;

wherein $R^1$ is a radical selected from the group consisting of methyl, ethyl, propyl, isopropyl, butyl, isobutyl, tert-butyl, pentyl, isopentyl, neopentyl, hexyl, isohexyl, heptyl, isoheptyl, octyl, isoctyl, cyclohexylmethyl, cyclohexylethyl, benzyl, phenylethyl, cyclopropyl, cyclobutyl, cyclopentyl, cyclohexyl, cycloheptyl, cyclooctyl, and adamantyl, vinyl, allyl, 2-phenylethenyl, 2-furylethenyl, 2-pyrrolyl-ethenyl, 2-pyridylethenyl, 2-thienylethyl, ethynyl, propargyl, tolyl, 4-methoxyphenyl, 3,4-dimethoxyphenyl, 4-fluorophenyl, 4-trifluoromethylphenyl, 4-chlorophenyl, naphthyl, furyl, pyrrolyl, pyridyl, cyclopentenyl, cyclohexenyl, cycloheptenyl, oxiranyl, pyrrolidinyl, piperidinyl, tetrahydrofuryl, tetrahydropyranyl, dihydrofuryl, dihydropyrrolyl, dihydropiranyl, and dihydropyridyl.

3. The compound according to the claim 1 wherein $R^1$, $R^2$ and R are independently a straight chain or branched alkyl radical having 1 to 10 carbon atoms, a straight chain or branched alkenyl radical having 2 to 10 carbon atoms, or a straight chain or branched alkynyl radical having 2 to 10 carbon atoms, a cycloalkyl radical having 3 to 10 carbon atoms, a heterocycloalkyl radical having 3 to 10 carbon atoms, a cycloalkenyl radical having 3 to 10 carbon atoms, a heterocycloalkenyl radical having 3 to 10 carbon atoms, a polycycloalkyl radical having 6 to 20 carbon atoms, an aryl radical having 6 to 20 carbons, a heteroaryl radical having 3 to 15 carbon atoms;

or $R^2$ is RO—, RS— or RR'N— radical wherein R is as defined above,

R' is a hydrogen or R as defined above; R and R' can be connected to form a cyclic structure which has 2 to 10 carbon atoms;

$R^3$, $R^4$, $R^5$ or $R^6$ are each hydrogen or an acyl radical having 1 to 20 carbons or R as defined above or a hydroxyl protecting group;

$R^7$ is an acyl group having 1 to 20 carbons;

$R^8$ is a hydrogen or a hydroxyl protecting group.

4. The compound according to claim 1 wherein $R^1$ is a tolyl, 4-methoxyphenyl, 3,4-dimethoxyphenyl, 4-fluorophenyl, 4-trifluoromethylphenyl, 4-hydroxyphenyl,1-naphthyl, 2-naphthyl, pyridyl, furyl, thienyl, pyrrolyl, N-methylpyrrolyl, 2-phenylethenyl, 2-furylethenyl, 2-pyridylethenyl, 2thienylethenyl, 2-phenylethyl, 2-cyclohexylethyl, cyclohexylmethyl, isobutyl or cyclohexyl;

$R^2$ is selected from the group consisting of phenyl, tolyl, 4-fluorophenyl, 4-chlorophenyl, 4-methoxyphenyl, biphenyl, 1-naphthyl, 2-naphthyl, isopropyl, isobutyl, neopentyl, hexyl, heptyl, cyclohexyl, cyclohexylmethyl, benzyl, phenylethyl, and phenylethenyl;

or $R^2$ is RO— wherein R is selected from the group consisting of a methyl, ethyl, propyl, isopropyl, butyl, isobutyl, tert-butyl, pentyl, isopentyl, neopentyl, hexyl, isohexyl, cyclohexyl, phenyl, benzyl and 9-fluorenylmethyl;

or $R^2$ is RR'N— selected from the group consisting of a methylamino, ethylamino, propylamino, isopropylamino, butylamino, isobutylamino, tert-butylamino, neopentylamino, cyclohexylamino, phenylamino or benzylamino, dimethylamino, diethylamino, dipropylamino, dibutylamino, dipentylamino, dihexylamino, dicyclohexylamino, methyl(tert-butyl)amino, cyclohexyl(methyl)amino, methyl(phenyl)amino, pyrrolidiono, piperidino, or morpholino group;

$R^3$ and $R^4$ are selected from the group consisting of a hydrogen, acetyl, chloroacetyl, dichloroacetyl, trichloroacetyl, and trifluoroacetyl, benzoyl, phenylacetyl, acryloyl, and crotyl, cinnamoyl, allyl, benzyl, methoxymethyl, methoxyethyl, 1-ethoxyethyl, tetrahydropyranyl, 2,2,2-trichloroethoxylcarbonyl, benzyloxycarbonyl, tert-butoxycarbonyl, 9-fluroenylmethoxycarbonyl, trimethylsilyl, triethylsilyl, (tert-butyl)dimethylsilyl;

$R^5$ is selected from the group consisting of a hydrogen, acetyl, chloroacetyl, allyl, benzyl, acryloyl, crotyl, and cinnamoyl and $R^6$ is a hydrogen; wherein $R^5$ and $R^6$ are connected to form a cyclic structure selected from the group consisting of carbonyl, propylidene, butylidene, pentylidene, phenylmethylidene, dimethylmethylidene, diethylmethylidene, dipropylmethylidene, dibutylmethylidene, methoxymethylidene, ethoxymethylidene, methylene, ethylene, and propylene;

$R^7$ is selected from the group consisting of benzoyl and cyclohexanecarbonyl;

$R^8$ is selected from the group consisting of a hydrogen, 1-ethoxyethyl, 2,2,2-trichloroethoxylcarbonyl, trimethylsilyl, triethylsilyl, and tert-butyldimethylsilyl.

5. The compound according to claim 4 wherein $R^1$ is a phenyl, 4-methoxyphenyl, 3,4-dimethoxyphenyl, 4-fluoromethyl, 4-trifluoromethylphenyl, furyl, 2-phenylethenyl, 2-phenylethyl, 2-cyclohexylethyl, 2-furylethenyl, 2-phenylethyl, 2-cyclohexylethyl, cyclohexylmethyl or cyclohexyl;

$R^2$ is selected from the group consisting of phenyl, tolyl, 4-methoxyphenyl, biphenyl, 1-naphthyl, 2-naphthyl, isobutyl, pentyl, neopentyl, hexyl, cyclohexyl, cyclohexylmethyl, benzyl, phenylethyl, and phenylethenyl;

or $R^2$ is RO— wherein R is selected from the group consisting of a methyl, ethyl, butyl, tert-butyl, cyclohexyl, phenyl, and benzyl;

or $R^2$ is RR'N— selected from the group consisting of an ethylamino, tert-butylamino, phenylamino, benzylamino, dimethylamino and morpholino group;

$R^3$ is a hydrogen, triethylsilyl or 2,2,2-trichloroethoxylcarbonyl;

$R^4$ is a hydrogen, acetyl or 2,2,2-trichloroethoxylcarbonyl;

$R^5$ is an acetyl; $R^6$ is a hydrogen; and
$R^5$ and $R^6$ are connected to form a carbonate;
$R^7$ is benzoyl or cyclohexanecarbonyl;
$R^8$ is a hydrogen, 1-ethoxyethyl, triethylsilyl, or tert-butyldimethylsilyl.

6. The compound according to claim 4 wherein
$R^1$ is a alkyl;
$R^2$ is phenyl or tert-butoxy;
$R^3$ is a hydrogen, triethylsilyl or 2,2,2-trichloroethoxylcarbonyl;
$R^4$ is a hydrogen, acetyl or 2,2,2-trichloroethoxylcarbonyl;
$R^5$ is an acetyl and $R^6$ is a hydrogen;
or $R^5$ and $R^6$ are connected to form a carbonate;
$R^7$ is benzoyl;
$R^8$ is a hydrogen or 1-ethoxyethyl.

7. A pharmaceutical composition having antineoplastic activity comprising the compound of claim 1 and a physiologically acceptable carrier therefor.

8. A method for treating tumors selected from the group consisting of ovarian, breast, non-small cell lung and colon cancer which comprises administering to a patient an effective antitumor amount of the compound of claim 1.

* * * * *

UNITED STATES PATENT AND TRADEMARK OFFICE
CERTIFICATE OF CORRECTION

PATENT NO. : 5,475,011
DATED : December 12, 1995
INVENTOR(S) : Uwao Ojima, et. al.

It is certified that error appears in the above-identified patent and that said Letters Patent is hereby corrected as shown below:

Title page, item [73], Assignee: add -- Indena SpA Gruppo Inverni Della Beffa --.

Signed and Sealed this

Thirtieth Day of March, 1999

Attest:

Q. TODD DICKINSON

*Attesting Officer*    *Acting Commissioner of Patents and Trademarks*